United States Patent
Nakamura

(10) Patent No.: US 6,649,397 B1
(45) Date of Patent: Nov. 18, 2003

(54) MICROBIAL CULTURE LIQUORS CONTAINING MICROORGANISMS DIFFERING IN CHARACTERISTICS AND LIVING IN SYMBIOSIS AND METABOLITES THEREOF, CARRIERS AND ADSORBENTS CONTAINING THE ACTIVE COMPONENTS OF THE CULTURE LIQUORS AND UTILIZATION OF THE SAME

(75) Inventor: Keijiro Nakamura, Hino (JP)

(73) Assignee: Orient Green Co., Ltd., Tokyo (JP)

( * ) Notice: Subject to any disclaimer, the term of this patent is extended or adjusted under 35 U.S.C. 154(b) by 0 days.

(21) Appl. No.: 09/673,655

(22) PCT Filed: May 6, 1999

(86) PCT No.: PCT/JP99/02346

§ 371 (c)(1),
(2), (4) Date: Jan. 5, 2001

(87) PCT Pub. No.: WO99/57243

PCT Pub. Date: Nov. 11, 1999

(30) Foreign Application Priority Data

| May 6, 1998 | (JP) | 10-159799 |
| Jun. 1, 1998 | (JP) | 10-187993 |
| Jun. 8, 1998 | (JP) | 10-194906 |
| Jul. 21, 1998 | (JP) | 10-237920 |
| Jul. 28, 1998 | (JP) | 10-244323 |
| Jul. 28, 1998 | (JP) | 10-244324 |
| Aug. 1, 1998 | (JP) | 10-250301 |
| Aug. 25, 1998 | (JP) | 10-279282 |
| Sep. 9, 1998 | (JP) | 10-294400 |
| Oct. 5, 1998 | (JP) | 10-316764 |
| Jan. 4, 1999 | (JP) | 11-033348 |
| Mar. 9, 1999 | (JP) | 11-105704 |
| Apr. 26, 1999 | (JP) | 11-156926 |

(51) Int. Cl.[7] .............................................. C12N 1/00
(52) U.S. Cl. .................... 435/243; 435/252.1; 435/262; 435/262.5
(58) Field of Search .................... 435/243, 252.1, 435/262, 262.5

(56) References Cited

FOREIGN PATENT DOCUMENTS

| JP | 55-86593 | 6/1980 |
| JP | 60-27672 | 2/1985 |
| JP | 60-137492 | 7/1985 |
| JP | 3-72879 | 3/1991 |
| JP | 5-244962 | 9/1993 |
| JP | 5-252842 | 10/1993 |
| JP | 6-71293 | 3/1994 |
| JP | 6-239608 | 8/1994 |
| JP | 7-48193 | 2/1995 |
| JP | 7-274942 | 10/1995 |
| JP | 8-24828 | 1/1996 |
| JP | 8-119780 | 5/1996 |
| JP | 8-196265 | 8/1996 |
| JP | 8-209669 | 8/1996 |
| JP | 8-252086 | 10/1996 |
| JP | 8-277002 | 10/1996 |
| JP | 8-280378 | 10/1996 |
| JP | 10-46146 | 2/1998 |
| JP | 10-155476 | 6/1998 |
| JP | 10-167921 | 6/1998 |

*Primary Examiner*—Leon B. Lankford, Jr.
(74) *Attorney, Agent, or Firm*—Arent Fox Kintner Plotkin Kahn

(57) ABSTRACT

Solutions containing microorganisms differing in characteristics from each other and living in symbiosis with each other and enzymes characterized by containing aerobic microorganisms, anaerobic microorganisms and at least one basidiomycete belonging to the family Pleurotaceae living in symbiosis, metabolites thereof and enzymes; carriers obtained by adsorbing the components of the above solutions onto finely ground carbonaceous materials; and porous materials obtained by adsorbing the components of the above solutions onto porous materials. Because of having various effects of absorbing, adsorbing and decomposing harmful matters, deodorizing, decolorizing, etc., these materials are applicable to various uses in the fields of agriculture and environment.

31 Claims, 4 Drawing Sheets

(a)

(b)

MICROBIAL CULTURE LIQUORS CONTAINING MICROORGANISMS DIFFERING IN CHARACTERISTICS AND LIVING IN SYMBIOSIS AND METABOLITES THEREOF, CARRIERS AND ADSORBENTS CONTAINING THE ACTIVE COMPONENTS OF THE CULTURE LIQUORS AND UTILIZATION OF THE SAME

DETAILED DESCRIPTION OF THE INVENTION

1. Field of the Invention

The present invention relates to microbe cultures, a process for producing the same, and utilization thereof. More particularly, the invention relates to microbe cultures containing anaerobic and aerobic microbes, which cannot hitherto live in symbiosis with each other, living in symbiosis with each other, and enzymes, which are metabolites of these microbes, the process for producing the same, carriers and absorbing materials containing the active ingredients of the culture and their applications to agricultural and environmental fields.

2. Background Arts

In recent years, applications of microbes to agricultural and environmental fields have received considerable attention from ecological viewpoint.

Attempts have been made to apply soil improving materials based on microbe technologies to soil which has become exhausted due to the use of a large amount of agricultural chemicals, and dormant soil in crop rotation.

For example, Japanese Examined Patent Publication No. 4-42355 discloses that a mixture obtained by injecting root nodule bacteria and Azotobacter or photosynthetic bacteria and Thiobacillus to a culture comprising an aqueous sterile plant solution having sucrose or maltose added thereto, cultivating the bacteria at approximately 25 C., and mixing the culture with a separately prepared culture composed of nitrifying bacteria, yeast, thermophiles, *Bacillus subtilis*, and bacteria belonging to Pseudomonas has the ability to accelerate thermal maturing, to increase the effects of fertilizer, to make remaining chemicals harmless, and to suppress insects causing damage to crops.

However, the conventional method is disadvantageous in that the soil to which it can be applied is restricted to soil stained by chemicals or dormant soil in crop rotation, and yeast which can be used is also restricted to that from rice bran. In addition, it takes a very long period of time to return the soil to normal soil.

Recently, the environment is increasingly being destroyed due to desertification or acidic rains, and such phenomena have become worldwide problems.

In order to plant such an exhausted area with trees, an effort has been made to plant trees by placing a high water absorbing polymer as a base material, and applying water to the base material in order to grow trees. However, the high water absorbing polymer is expensive and plants to be applied are restricted. In addition, the soil which has been desertified is never returned to the original soil.

Similarly, man-made destruction of the environment such as that due to slash and burn farming and haphazard deforestation creates serious problems in terms of plant environment. No process has yet been found in which the soil whose crumb structure has been lost due to the man-made destruction of environment can be returned to the original state.

Moreover, there is a need to utilize soils containing salt such as a sandy beach, sandy soils such as residing around rivers, etc. as soils where desired crops can be planted, but there is no technique at present.

In addition to agriculture, gardening such as cultivating dwarf trees, gardening as a pastime, etc has become popularized. Ornamental plants, vegetables, herbs and other plants are cultivated not only by breeders but also household. In cultivating these plants, generally a solid medium for cultivating plants is incorporated into a container such as a flowerpot, a planter, and then seeds or tubers are embedded into the medium or young plants are transplanted.

However, the solid medium which has hitherto been utilized in the cultivation of such plants contains a considerable amount of insects carrying disease germs and eggs thereof, fungi, etc., which have an adverse influence upon the plants to be cultivated. Specifically, due to the eggs of insects, the insects themselves, or pathogenic bacteria, such as lead scald, powdery mildews, root knots, root rot, brown canker, rust and the like, plants often are infected from the solid medium such as soil. Depending upon the origin of the medium, the medium often contains agricultural chemicals and some other harmful substances. Moreover, insects etc. are oviposited into the medium or onto a plant during the cultivation of the plant, and the bred insects sometimes adversely affect the plant.

In order to eliminate such insects, mildews etc. existing on or into the solid medium, agricultural chemicals are conventionally applied to the medium. However, if the crumb structure inherent to the soil should be lost when the insects and harmful microorganisms are eliminated by the spraying of agricultural chemicals, this makes the soil inappropriate for the cultivation of plants. Particularly, in the case of the cultivation of plants in a container, excess water flows out when a plant in a container is watered; the agricultural chemicals unduly remain in the water which flows out. Further, in the case of the cultivation of edible plants, the agricultural chemicals cause an adverse effect to the human body.

When the plants are cultivated, solid or liquid fertilizers are incorporated into the medium. These fertilizers are mainly chemically synthesized fertilizers and thus, the medium in which chemical fertilizers are incorporated is greatly different from the original medium for cultivating the plants. In this case, the period of fertilization and the amount of fertilizer to be applied should be strictly controlled.

Similar to the cultivation of plants, solid media such as sawdust or decayed wood are used for cultivating mushrooms, and such medium also contains Eumycetes, insects, and their eggs.

Japanese Examined Patent Publication No. 4-42355 discloses the admixture of microorganisms with the medium or plants themselves. According to this publication, a mixture obtained by injecting root nodule bacteria and Azotobacter or photosynthetic bacteria and Thiobacillus to a culture comprising an aqueous sterile plant solution having sucrose or maltose added thereto, cultivating the bacteria at approximately 25 C., and mixing the culture with a separately prepared culture composed of nitrifying bacteria, yeast, thermophiles, *Bacillus subtilis*, and bacteria belonging to Pseudomonas has the ability to accelerate thermal maturing, to increase in effects of fertilizer, to make remaining chemicals harmless, and to suppress insects causing damage to crops.

However, in the application of such a group of bacteria there are disadvantages in that it takes a very long period of time to take the effect after the application of these bacteria, and that the effect is last only a short time. Also, the group of bacteria cannot be applied to a plant cultivated in a container.

Also, the solid medium after the cultivation of an annual plant or the solid medium after plants have been harvested cannot be utilized again if these bacteria are used.

Moreover, these bacteria do not have an effect to activate any withering plant.

Meanwhile, various processes for taking measures to cope with bad smells based on the functions of bacteria have been known.

For example, Japanese Unexamined Patent Publication No. 6-277684 discloses a process for deodorizing a bad smelling gas utilizing bacteria.

Also, Japanese Unexamined Patent Publication Nos. 51-129865, 53-58375, and 60-34799 disclose processes for decoloring and deodorizing sewage disposal, excreta, etc.

However, these processes are disadvantageous in requiring at least two stages, due to the use of different kinds of bacteria, i.e., anaerobic and aerobic bacteria.

In recent years, processes for treating waste water, for improving soils, etc. and insecticides utilizing Effective Microbes called EM which have living anaerobic bacteria and aerobic bacteria together with each other, mainly containing lactobacilli have been developed. However, substantially aerobic bacteria and facultative bacteria are used in EM and, thus the synergism of both bacteria is little. In the use of EM, fermentation material call EM material should be utilized and making the application of EM is severely restricted.

Meanwhile, a large amount of seston is contained in lakes, marshes, rivers, etc. Seston is a general term for granular substances suspended in water and indicates organic seston originated in floating living bodies and inorganic seston originated in earth and sand or particles. In many cases, sestons are together with each other to make up as agglomeration. The organic seston sometimes serves as a place habitable for small creatures. However, it changes the transparency of water for the worse, and becomes a factor in the generation of water blooms due to the rotting of the organic seston and, thus, it is desirable to remove the organic seston. The inorganic seston contained in exhaust water from chemical factories, etc. is a mass containing harmful substances and, it is also desirable to remove it.

Conventionally, in order to treat the water containing the seston, seston is aggregated by the use of a flocculant such as aluminum sulfate, and the seston is removed by the filtration of settling substances or floating substances. However, in the treatment utilizing such a flocculent, the flocculant utilized should be subjected to secondary treatment, and the performance of the flocculant is insufficient. Moreover, there is a possibility that the flocculant causes an adverse influence upon the ecologic system and, thus the use of the flocculant is not assumed to be a good method. In addition, since there are various kinds of water to be treated such as organic exhausts inclusive in the exhaust water from sewage disposal, exhaust water from food processing, exhaust water containing excreta such as pig-breeding and stockbreeding, and water from eutrophic lakes and marshes; inorganic exhausts such as exhaust water from chemical industries, there are various kinds of sestons, and they cannot be treated by one flocculant.

In treating water from a lake or marsh, the stage for removing harmful substances contained in the water, the stage for decoloration, and the deodorization stage should be required in addition to the removal of seston.

In light of the above situations, it is desired to develop a flocculant (1) that requires no secondary treatment such as removal of the flocculant; (2) that has no adverse influence upon the ecological system; (3) that can be widely applied irrelevant to the origin of the seston, i.e., organic and inorganic sestons; and (4) that can treat harmful substances, and decolor and deodorize subjective substances at the same time.

It is desirable that water blooms occurring onto and into the hydrosphere, which have been eutrophicified, be removed. Also, it is desirable to remove petroleum flowing in the sea area, for example, due to a shipping accident such as an accident of a tanker; thus, it is desirable to develop an effective treating means.

In addition, a biological treatment of filthy water containing excrements and urines exhausted from various stock-breeding fields such as pick-breeding fields, cowsheds, and chicken farms as well as household exhaust water, exhaust water from chemical industries, food industries and the like containing various components has recently drawn considerable attention.

For example, Japanese Unexamined Patent Publication Nos. 55-86593, 60-137492, 6-71293, 9-20678, and the like disclose processes of separately treating exhaust water with anaerobic bacteria and aerobic bacteria. However, these processes can only treat exhaust water in a restricted manner and are not assumed to be effective. No process has been developed which can treat pollutants originating from different sources all at once.

Efforts have been made to develop a biological process for converting harmful substances into harmless ones.

Many halogen compounds having chlorine or bromine, etc. are specified as specific chemical compounds and specified chemical compounds, and many of them are sources causing an environmental problem. Typical examples include halogenated aromatic compounds such as dioxins, polychlorobiphenyls, and chlorobenzenes; and aliphatic halogen compounds such as tetrachloroethylene, trichloroethylene, dichlorometahne, carbon tetrachloride, 1,2-dichloroethylene, 1,1-dichloroethylene, cis-1,2-dichloroethylene, 1,1,1-trichloroethane, and 1,1,2-trichloroethane, 1,3-dichloropropene.

Various suggestions have been made to decompose these organic halogen compounds based on the functions of bacteria.

With regard to the decomposition of organic aliphatic compounds, a process for removing an organic chlorine compound comprising injecting ammonia-oxidizing bacteria with a polluted portion contaminated with organic chlorine substances such as soil or contaminated groundwater to allow the contaminants to be in contact with the ammonium-oxidizing bacteria is described in Japanese Unexamined Patent Publication No. 10-180237.

A process for purifying a substance contaminated with organic chlorine compounds comprising declorinating the chlorine contaminating compounds under a reduction atmosphere under neutral conditions in the presence of at least one heterotrophic bacterium and iron is described in Japanese Unexamined Patent Publication No. 10-216694. The heterotrophic bacteria exemplified therein include metanogens (for example, Methanosarcina, Methanothrix, Methanobacterium, Methanobrevibacter, etc.); sulfate reduction bacteria (for example, Desulfovibrio, Desulfotomaculum, Desulfobacterium, Desulfobacte, Desulfococcus, etc); acid production bacteria (for example, Clostridium, Acetivibrio, Bacteroides, Ruminococcus, etc.) and facultative anaerobic bacteria (for example, Bacillus, Lactobacillus, Aeromonas, Streptococcus, Micrococcus, etc.).

However, such processes can only be applied to restricted systems such as soil and aqueous solutions, and are problematic in treating efficiency, cost, convenience, etc. In order to maintain the activity of the bacteria for the treatment, the temperature, pH level, nutrient salts, the amount of dissolved oxygen, and the like should be controlled in an appropriate manner and, thus, the process is disadvantageous when an apparatus is required for an environment where oxygen or nutrient salts are continuously being added.

As a process for decomposing an aromatic halogen compound, there is a process for decomposing PCBs utilizing microorganisms. However, the microorganisms which can be utilized depend upon the substitution position of chlorines, and the decomposition is imperfect, i.e., the conventional microorganisms can decompose PCB only to chlorobenzene. Also, the PCB decomposition utilizing the microorganisms can only be applied to a restricted area. The decomposition of other organic halogen compounds such as dioxins utilizing microorganisms has not yet been found, and these compounds are decomposed by a chemical or physical process.

Solids and liquids such as burned ash, soda glass, soil, exhaust liquid from semiconductor processing, and exhaust liquid from plating contain various kinds of heavy metals such as chromium, manganese, cobalt, nickel, zinc, lead, and mercury in various concentrations, and it is required that these metals are removed through the functions of microorganisms.

Furthermore, photographic exhaust liquids can also be mentioned as those which contains various harmful substances.

There are a series of stages from the development of photographic film to the printing of the developed film. First, a photographic film such as a negative film, positive film, or reversal film is developed, the developed film is fixed, washed with water, and dried to prepare a film for printing; thereafter, the developed film is printed onto print out paper. At present, photo-finishing service has been popularized in which these stages are carried out all at once.

Photographic films, print-out paper, and various solutions for treating them generally contain various chemicals such as a silver halide emulsion as a photosensitive material (e.g., silver bromide, silver iodide, silver iodide bromide, etc.); stabilizers (e.g., benzotriazole, azaindolysines, etc.); color sensitizers (e.g., orthochromatic, panchromatic sensitizers, super-panchromatic sensitizers etc.); hardening agents (e.g., aldehyde compounds, etc.).

Specifically, developing the film and printing the developed film onto the print-out paper are carried out via various stages such as a color developing stage, washing with running water, development adjustment and hardening, hardening, stopping, first fixation, washing with running water, second fixation, removal of water droplets, and drying, and various organic and inorganic compounds are used in each stage.

As described above, in developing the film and printing the developed film onto the print out paper, an exhaust liquid containing various compounds in which these compounds react with each other are discharged.

Depending upon the situation of the development, an auxiliary operation, for example, using chromium compounds such as potassium dichromate or mercury compounds such as mercuric chloride or a reducing operation, for example, by mixing potassium ferricyanide with sodium thiosulfate or potassium permamganate, is carried out in some cases.

As photography has been increasingly popularized and the frequency of taking photos has increased, the amount of the exhaust liquids has also increased significantly. However, with regard to the treatment of the exhaust liquid, although silver, which is a relatively expensive material, is recovered, since the compounds other than silver are of many kinds, the printing treatments depend upon the companies, and the concentration and kinds of the compounds are different according to the company, and no process for treating them which can decompose them all at once has yet been determined.

As a substance which requires conversion of chemical substances into harmless ones, porous absorbing material can be mentioned.

The porous absorbing materials represented by activated carbon have been utilized in various fields such as filters for water treatment or deodorizing filters, such as absorbing materials for treating harmful substances.

These absorbing materials exhibit their absorbing function by absorbing substances to be absorbed within many pores possessed by the absorbing material, but their function is decreased when a certain amount of the substances are absorbed.

The used porous absorbing materials are usually collected and recovered. In this case, the harmful substances absorbed are discharged out of the system. For this reason, it is necessary to take some measure to convert the discharged harmful substances, which are discharged out of the system, into harmless ones, requiring a huge cost.

At present, river sands have been utilized as fine aggregates, but the supply amount of the river sands has increasingly decreased. Also, the river sands themselves have been contaminated and, thus, contain various harmful substances.

In such a situation, there is a tendency that burned ash and waste glasses are, recycled for use as aggregates.

Since the burned ash contains harmful substances such as lead, zinc, other heavy metals, and organic chlorine compounds, these substances are treated and the burned ash is utilized as an aggregate in the form of slug. However, in some cases, harmful substances such as organic chlorine still remain in the burned ash even after the treatment and, thus, it is required to remove such hard-to-treat substances as a pretreatment. Also, in other cases, the removal of heavy metals in the burned ash is not sufficient enough. The burned ash can only be used as an aggregate having a large particle size, and cannot be utilized as a fine aggregate.

The process for pulverizing waste glasses into sands is problematic in that there are contents of impurities such as lead, and a high cost is required to carry out pulverization into fine aggregates.

Sands containing salts such as sea sands cannot be utilized as fine aggregates.

In recent years, a process has been developed for increasing the performance for purifying water such as that from sewage by the introduction of microorganisms into concrete. For example, there is a structural material comprising a cement and tourmaline with which Effective Microbe solution and EM material are admixed. However, this structural material utilizes expensive tourmaline, exhibits insufficient water purification performance, and requires the introduction of an EM material such as rice bran. Also, there is a disclosure that aggregates may be used instead of tourmaline. However, according to the examination, the effect of water purification in this case is worse in comparison with the use of tourmaline, and the effect obtained by the introduction of the microorganisms cannot be observed.

For this reason, aggregates which can impart water purification performance to the structural material are required.

As a possible field for making use of microorganisms, garbage treatment can be mentioned.

Wastes are generally classified into household wastes and business wastes, and these wastes are dumped into landfills or are burned in furnaces at present. However, the treatment of the waste becomes serious in terms of making the landfill safe, treating harmful gases discharged from the furnaces, and treating harmful substances contained in the burned ash.

Of these wastes, it is said that approximately 60% of wastes are made up of garbage such as leftovers and residues of cooking. Also, a large amount of garbage is discharged from restaurants, grocers, grocery stores, convenience stores, inns, hotels, hospitals, etc. It is said that approximately 30% of wastes are garbage originating both from households and businesses.

Consequently, an effective treatment of the garbage is a very serious problem in terms of the treatment of the wastes and becomes one of the most important problems in many local self-governing bodies.

As one effective treatment of the garbage, processes for treating garbage based on the functions of the decomposition and fermentation of the garbage by microorganisms can be mentioned.

These process for treating garbage utilizing microorganisms are roughly divided into (1) a process for converting the garbage into compost; and (2) a process of decreasing the volume of the garbage or essentially eliminating garbage by decomposing the garbage into $CO_2$ and $H_2O$.

The process for converting the garbage into compost is carried out in a container for conversion into compost called a composter or a so-called compo-planter, serving the composter and a planter at the same time. The composter is composed of a body of container comprising a vent, a space, a heat-retention layer, and a cap. First, a medium (medium for cultivation) such as chaff is spread over the interior of the body; garbage is then spread over the medium at approximately the same depth as the medium; and a material containing Bacillus, actinomycete, etc. is incorporated thereon. The medium and garbage are alternatively laminated to promote the fermentation of the garbage in order to carry out the conversion of the garbage into compost. After approximately 1 month, the garbage in the composter is fermented to produce compost.

The process for converting garbage into compost utilizing microorganisms can be carried out in the inexpensive installation as described above, but it unduly takes 1 month or more for the conversion of the garbage into compost, and the amount of the garbage which can be utilized in one treatment is restricted. Moreover, the fertilizer resulting in the treatment of the garbage smells bad, and the application of the fertilizer thus obtained sometimes causes the generation of Fusarium.

On the other hand, an apparatus for treating a relatively small amount of garbage utilizing microorganisms has been developed for use in households, restaurants, etc. This apparatus is mainly composed of a sealable container equipped with a vent, a heat-retention layer, an aeration means, a drain and a stirrer, and the bottom of the container is divided by a porous plate. A material for improving the breathability is spread over the porous plate, over which sawdust etc. is spread for the purpose of making a residence for microorganisms and adjusting the water contained in the garbage. Predetermined microorganisms are incorporated into the container, the garbage is thrown in the container, the container is sealed, and the contents are mixed with aeration being carried out by means of a vent such as a pump, whereby the garbage is decomposed into carbon dioxide and water to decrease the volume of the garbage.

According to this apparatus, approximately one kilogram of garbage can be treated daily. However, the ratio of decrease in the actual garbage is as low as from 60 to 80%. Also, the media and microorganisms utilized should be replaced every 3 to 4 months. In this apparatus, sulfurous acid, nitrogen oxides, etc. which should be removed occur in the decomposition of the garbage, and the device for removing them is very expensive.

An apparatus for decreasing a large volume of garbage has also been developed. This apparatus is composed of approximately a 500–600 liter volume sealable container having a stirring means, a vent, a deodorizing means, etc. The container is substantially filled with wooden chips such as cedar chips as a material. Then, approximately 20 kg of the garbage is incorporated into the container, the contents are intermittently mixed while supplying 100 to 300 liters of air per minute to decompose the garbage with the microorganisms contained in the chips.

However, such an apparatus for decreasing a large volume of garbage is very expensive, and sulfurous acid, nitrogen oxides, etc. which should be removed occur in the decomposition of the garbage, similar to the case of the small size apparatus described above.

As described above, the processes for converting garbage into compost leave something to be improved.

Meanwhile, many efforts have been made to convert seawater into freshwater. As processes for converting seawater into freshwater, a multiple flushing process, a multiple effect evaporation, and a reverse osmosis process can be mentioned. The multiple flushing process and the multiple effect evaporation are effective on a very large scale such as construction of a national plant, but the reverse osmosis process, which requires only a small investment in plant and equipment, has been popularized.

As processes for converting seawater into freshwater utilizing reverse osmosis, Japanese Unexamined Patent Publication No. 10-128325 discloses a process for obtaining freshwater having a low concentration of boron by running seawater through two reverse osmosis apparatuses placed in series by means of one pump; Japanese Unexamined Patent Publication No. 10-128325 discloses an apparatus for converting seawater into freshwater composed of a reverse osmosis module, and a storage pump for pumping water produced in a water collecting pipe of the reverse osmosis.

However, these processes for converting seawater into freshwater by the reverse osmosis require a large amount of energy and complicated equipment. Also, in such processes, the amount which can be treated has severely restricted. Furthermore, the reverse osmosis itself is very expensive and the maintenance of the apparatus requires high costs.

Consequently, in addition to these approaches, there is a demand for developing a process for converting seawater into fresh water on the basis of the function of microorganisms.

As described above, microorganisms can be applied to various field in a wide variety of manners. However, in the field expected to benefit from the application of microorganisms, there has not yet been any technique which has been completed, or such a technique said to be completed only has a small effect.

From such viewpoints, as one expected group of microorganisms, a culture containing anaerobic microorganisms and aerobic microorganisms living together with each other filed by the present inventor as Japanese Patent Application No. 9-291467 can be mentioned. In this patent application, a suggestion has been made to convert chemical hazards such as dioxins into harmless substances through the function of the culture. However, the group of the microorganisms contained therein leaves something to be improved in terms of the productivity of cellulase and reducing power. Furthermore, there is a demand to utilize the group of the microorganisms as carried on a carrier.

SUMMARY OF THE INVENTION

Consequently, an object of the present invention is to determine microbiological techniques applicable to these applications and to provide microorganisms and metabolites having good effects in agricultural fields and environmental fields.

Another object of the present invention is to provide a process for applying these microorganisms and metabolites to these agricultural fields and environmental fields.

Still another object of the present invention is to find a novel process which apply these microbiological techniques.

The present invention concerns the following items:

1. A microorganism culture containing (a) aerobic microorganisms, (b) anaerobic microorganisms, (c) at least one Basidiomycetes belonging to *Pleurotus coruncopiae,* living in symbiosis with each other, and enzymes produced as their metabolites.
2. The microorganism culture as described in the above Item (1), wherein Basidiomycetes is obtained by mating *Pleurotus coruncopiae* with *Pleurotus coruncopiae.*
3. The microorganism culture as described in the above Item (1), which further contains photosynthetic bacteria.
4. The microorganism culture as described in the above Item (3), which further contains enzymes for decomposing carbon.
5. A process for producing the microorganism culture as described in the above Item (1), which comprises the following stages:
   (1) incorporating a source of aerobic microorganisms and an essence of Basidiomycetes containing at least *Pleurotus coruncopiae* into a solution obtained by pulverizing proteins mainly comprising animal proteins, adding grain and yeast to the pulverized substances to undergo fermentation, heating the fermented products, pulverizing the heated product, adding a Lactobacillaceae culture or a *Bacillus subtilis* culture to the pulverized products and fermenting the culture under aerobic conditions, and culturing the microorganisms under aerobic conditions at normal temperature and normal pressure until the solution becomes transparent; and
   (2) incorporating a source of anaerobic microorganisms to the above culture and culturing the mixture under anaerobic conditions at normal temperature and normal pressure.
6. A process for producing the microorganism culture as described in the above Item (3), which comprises the following stages:
   (1) incorporating a source of aerobic microorganisms and an essence of Basidiomycetes containing at least *Pleurotus coruncopiae* into a solution obtained by pulverizing proteins mainly comprising animal proteins, adding grain and yeast to the pulverized substances to undergo fermentation, heating the fermented products, pulverizing the heated product, adding a Lactobacillaceae culture or a *Bacillus subtilis* culture to the pulverized products and fermenting the culture under aerobic conditions, and culturing the microorganisms under aerobic conditions at normal temperature and normal pressure until the solution becomes transparent;
   (2) incorporating a source of anaerobic microorganisms to the above culture and culturing the mixture under anaerobic conditions at normal temperature and normal pressure, and
   (3) adding photosynthetic bacteria to the culture and further continuing the culturing.
7. A process for producing the microorganism culture as described in the above Item (4), which comprises the following stages:
   (1) incorporating a source of aerobic microorganisms and an essence of Basidiomycetes containing at least *Pleurotus coruncopiae* into a solution obtained by pulverizing proteins mainly comprising animal proteins, adding grain and yeast to the pulverized substances to undergo fermentation, heating the fermented products, pulverizing the heated product, adding a Lactobacillaceae culture or a *Bacillus subtilis* culture to the pulverized products and fermenting the culture under aerobic conditions, and culturing the microorganisms under aerobic conditions at normal temperature and normal pressure until the solution becomes transparent;
   (2) incorporating a source of anaerobic microorganisms to the above culture and culturing the mixture under anaerobic conditions at normal temperature and normal pressure,
   (3) adding photosynthetic bacteria to the culture and further continuing the culturing.
   (4) adding a carbon source originating from plants to the culture and further continuing the culturing, and
   (5) diluting the culture obtained in Stage (4) 2 to 4 times with the culture obtained in Stage (3).
8. A carbonaceous carrier containing microorganisms and enzymes originating from these microorganisms contained in the culture of the above Item (4) in a dissolved carbon.
9. A process for producing the carrier of the above Item (8), which comprises impregnation of finely divided carbon with the culture of the above Item (4) or its diluted solution diluted with water to incorporate the active components of the culture of the above Item (4) and at the same time to dissolve the carbon.
10. A porous absorbing material containing microorganisms and enzymes originating from these microorganisms contained in the culture of the above Item (4).
11. The porous absorbing material of the above Item (10), wherein the porous absorbing material is based on an activated carbon.
12. A process for producing the porous absorbing material of the above Item (11), which comprising impregnation of a porous absorbing material with the culture of the above Item (4) or its diluted solution diluted with water to incorporate the active components of the culture of the above Item (4).
13. The process for producing the porous absorbing material of the above Item (12), wherein the porous absorbing material is based on an activated carbon.

14. The process for producing the porous absorbing material of the above Item (12), wherein said porous absorbing material is a used material, and the material is impregnated with the culture of the above Item (4) or its diluted solution diluted with water for a period sufficient for decomposing the ingredients absorbed into the porous absorbing material to simultaneously carry out the recovery of the used porous absorbing material.

15. A filter containing the porous absorbing material of the above Item (10).

16. A soil improving material obtained by spraying or impregnating in the microbiological culture of any of the above Items (1) to (4) a fibrous substance originating from plants.

17. The soil improving material of the above Item (16), wherein said fibrous substance originating from plants is sawdust of needle leaf trees, pulverized substances of logged trees, rice chaff, buckwheat chaff, construction material having been primarily treated, or a mixture thereof.

18. A process for improving soil which comprises mixing the soil improving material of the above Item (16) or (17) with a fertilizer, and placing the mixture on soil to be treated at a height of from 1 to 100 cm.

19. The process of the above Item (18), wherein said soil to be treated is soil whose crumb structure has been lost.

20. The process of the above Item (18), wherein said soil to be treated is desertified soil or soil containing salts.

21. A process for improving soil which comprises placing a fibrous substance originating from plants mixed with a fertilizer at a height of from 1 to 100 cm, and spraying the culture of any of the above Items (1) to (4) or its diluted solution diluted with water.
22. The process as described in the above Item (21), wherein said soil to be treated is soil whose crumb structure has been lost.
23. The process as described in the above Item (21), wherein said soil to be treated is desertified soil or soil containing salts.
24. A process for optimizing a plant system composed of a container for cultivating a plant, a medium for cultivating a plant, and a plant to be cultivated; which process comprises:
   incorporating said plant system into a sealed container, filling the sealed container with the culture of any of the above Items (1) to (4) diluted with water, sealing the sealed container, and leaving the sealed container stand for a period sufficient for killing disease carriers and eggs thereof existing in the system.
25. The process for optimizing a plant system as described in the above Item 24, wherein said plants to be cultivated are somewhat withered, and the revival of the plants is carried out at the same time.
26. A process for reviving a plant attacked by a pathogenic organism, which comprises:
   (a) a stage of digging up the plant, and washing the whole of the plant with a solution of the microorganism culture described in any of the above Items (1) to (4) diluted with water,
   (b) a stage of spraying a solution of the microorganism culture described in any of the above Items (1) to (4) diluted with water on the soil thus dug, and
   (c) a stage for newly planting the plant and applying soil in which a solution of the microorganism culture described in any of the above Items (1) to (4) diluted with water is impregnated.
27. The process for reviving a plant as described in the above Item (26), wherein said plant is injured by stem canker, and which process further comprises a stage of surgically removing the portion infected with the stem canker, applying the slurry of the above Item (8), followed by drying.
28. The process for reviving a plant as described in the above Item (26), wherein said a pathogenic organism causes drop (*Sclerotinia sclerotiorum*), clubroot, mottled spot, brown canker, mildew, and rust.
29. An organic fertilizer obtained by adding feces and urine of livestock to a solution of the microorganism culture described in any of the above Items (1) to (4) diluted with water.
30. The fertilizer as described in the above Item (29), which has sawdust of needle leaf trees further added.
31. The process for improving soil as described in the above Item (29), wherein the fertilizer comprises the fertilizer as described in any of the above Items (18) to (21).
32. A garbage decomposing material obtained by impregnating fibrous substances originating from plants with a solution of the microorganism solution as described in any of the above Items (1) to (4).
33. The garbage decomposing material as described in the above Item (32), wherein said fibrous substances originating from plants contain hard-to-decompose substances.
34. A process for treating garbage which composes: incorporating garbage to be treated into the garbage treating material as described in the above Item (32) or (33), and stirring the mixture to decompose the garbage in an odorless manner.
35. A liquid fertilizer comprising an odorless liquid obtained from the process of the above Item 34.
36. A process for treating solid substances containing harmful substances or salts which comprises: mixing the carrier of the above Item (8) with the solid to be treated, and stirring the mixture, followed by washing with water.
37. The process as described in the above Item (36), wherein said solid substances to be treated are sands containing harmful substances or salts.
38. The process as described in the above Item (36), wherein said solid substances to be treated are burned ash or fly ash containing harmful substances.
39. A fine aggregate comprising the sand treated according the process of the above Item (37).
40. A reduction type construction material obtained from the fine aggregate of the above Item (39).
41. A fine aggregate comprising the burned ash or fly ash treated in the process of the above Item (38).
42. A reduction type construction material obtained from the fine aggregate of the above Item (41).
43. A reduction type construction material comprising the carrier of the above Item (8).
44. A process for removing water bloom which comprises spraying a solution of the microorganism solution as described in any of the above Items (1) to (4) diluted with water onto water bloom caused by eutrophication.
45. A process for treating seston which comprises incorporating the carrier of the above Item (8) into water containing seston to aggregate the seston.
46. A process for treating water containing polluted sediments comprising incorporating the carrier of the above Item (8) into water containing polluted sediments to decompose the polluted sediments.
47. An aggregating agent comprising the carrier of the above Item (8).
48. A process for treating a liquid containing salts which comprises passing water containing salts through a filter containing the absorbing material of the above Item (15) once or more times to remove the salts.
49. A process for treating a liquid containing salts which comprises incorporating the carrier of the above Item (8) into water containing salts, followed by stirring.
50. The process of the above Item (49) or (50), wherein said water contains seawater, and conversion of seawater into freshwater is carried out.
51. A process for treating a liquid containing harmful substances which comprises incorporating the carrier of the above Item (8) into a liquid containing harmful substances.
52. A process for treating a liquid containing harmful substances which comprises incorporating the carrier of the above Item (8) into a liquid containing harmful substances, followed by stirring.
53. A process for treating a liquid containing harmful substances which comprises passing a liquid containing harmful substances through a filter containing the absorbing material of the above Item (15) once or more times to remove the salts.
54. A process for treating a liquid containing harmful substances which comprises:
   a) incorporating the carrier of the above Item (8) into a liquid containing harmful substances, and
   b) passing the liquid containing harmful substances through the filter of the above Item (15) containing the absorbing material once or more times to remove the salts.
55. The process of the above Item (54), wherein Stage (a) is carried out while stirring.
56. The process described in any of the above Items (51) to (55), wherein said liquid containing harmful substances is an exhaust liquid containing heavy metals, organic halogen compounds or petroleum, an exhaust liquid from plating, an exhaust liquid from semiconductor processing, an exhaust liquid from developing photos, an exhaust liquid containing dyestuffs, exhaust water from sewage, and an exhaust liquid containing the mixtures of harmful substances.
56. An apparatus for treating a liquid comprising:
   an inlet for supplying water to be treated,
   a filtering portion comprising the filter of the above Item (15) containing at least one absorbing material, and
   a receiver which stores the treated water.
57. The apparatus of the above Item (56) which further comprises means for supplying the treated liquid to said filter, which is connected to the receiver, whereby the treated water is supplied to the filter after several treatment to recover the filter.
58. The apparatus of the above Item (56) or (57), which further comprises a water tank having a stirring portion for a pretreatment, and a transportation means for transporting the pretreated water to the filtering portion.
59. A process for treating a gas which comprises: a solution of the microorganism solution as described in any of the above Items (1) to (4) diluted with water to a gas to be treated.
60. A process for treating a gas which comprises the absorbing material of the above Item (15).
61. The process of the above Item (59) or (60), wherein the gas to be treated is selected from among bad smells originating from organic or inorganic compounds, and gases containing organic or inorganic chemical hazards.
62. A deodorizer comprising a solution of the microorganism solution as described in any of the above Items (1) to (4) diluted with water.
63. A liquid agent for decolorization of a liquid comprising a solution of the microorganism solution as described in any of the above Items (1) to (4) diluted with water.
64. A process for removing harmful substances from a construction material which comprises spraying or impregnating a construction material with a solution of the microorganism solution as described in any of the above Items (1) to (4) diluted with water.
65. A mildew-proofing agent comprising a solution of the microorganism solution as described in any of the above Items (1) to (4) diluted with water.
66. An agent for reviving plants comprising a solution of the microorganism solution as described in any of the above Items (1) to (4) diluted with water.
67. A deodorizer comprising the carrier of the above Item (4).
68. A deodorizer comprising the absorbing material of the above Item (10).
69. A filter for treating water comprising the filter of above Item (15) containing the absorbing material.
70. An apparatus for purifying water comprising the filter of the above Item (15) containing the absorbing material.
71. A showerhead comprising the filter for treating water of the above Item (69).
72. A water-purifying agent comprising the carrier of the above Item (8).
73. A water-purifying agent comprising the absorbing material of the above Item (10).

BRIEF DESCRIPTION OF THE DRAWINGS

FIGS. 4(a) to 4(b) each shows a graph for comparing the absorbing performance of the absorbing material of the present invention with that of the conventional material, wherein FIG. 4(a) is a graph showing the results of absorbing formaldehyde into the absorbing material of the present invention; FIG. 4(b) is a graph showing the results of absorbing formaldehyde into the conventional absorbing material; FIG. 4(c) is a graph showing the results of absorbing ammonia into the absorbing material of the present invention; and FIG. 4(d) is a graph showing the results of absorbing ammonia into the conventional absorbing material.

BEST MODES FOR CARRYING OUT THE INVENTION

Figure 1:
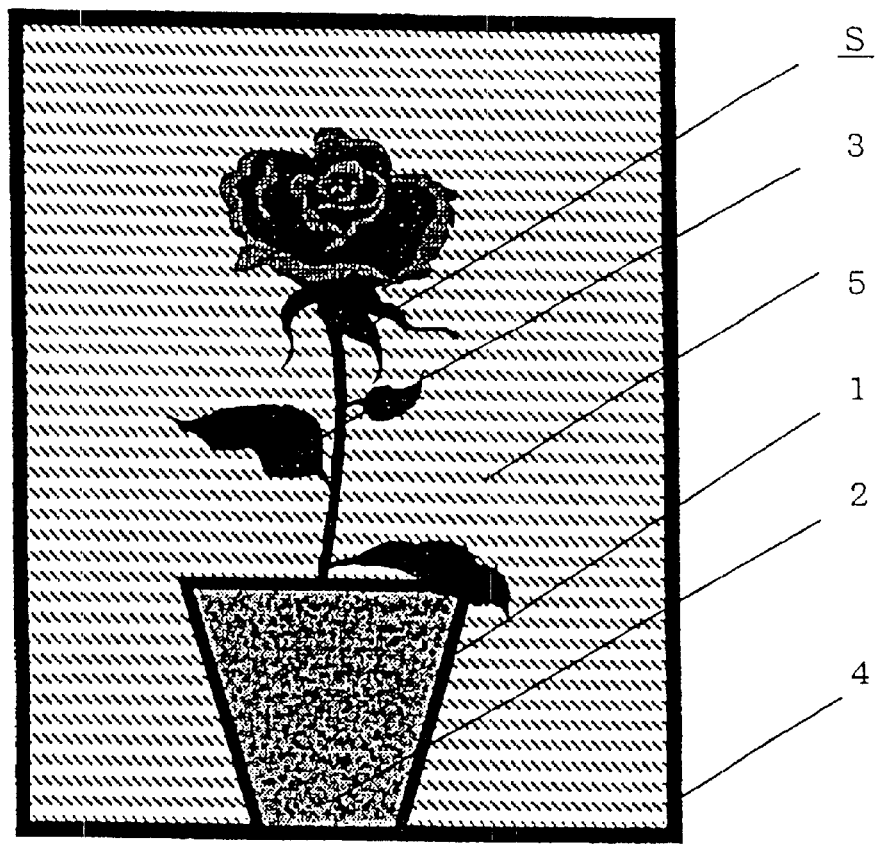
FIG. 1 is a cross sectional view showing one example of an apparatus for treating insects according to one embodiment of the present invention.

The present invention will now be described in detail.
Mixture of Microorganisms and Enzymes (OME)

According to the first aspect of the present invention, there is provided a microorganism culture containing (a) aerobic microorganisms, (b) anaerobic microorganisms, (c) at least one Basidiomycetes belonging to *Pleurotus coruncopiae*, living in symbiosis with each other, and enzymes produced as their metabolites (hereinafter referred to as "OM"), and a microorganism culture of OM which further comprising a carbon decomposing enzyme by the addition of a carbon source originating from plants to OM (hereinafter referred to as "OME").
(Organism Active Agent)

In preparation of OME according to the present invention, first a source of aerobic microorganisms and an essence of Basidiomycetes at least containing *Pleurotus coruncopiae* are cultured in a microorganism active agent under aerobic conditions, i.e., under aeration at normal temperature and at normal pressure for from two to five weeks, preferably from 20 to 30 days. The organism active agent used herein is prepared by (1) pulverizing proteins mainly comprising animal proteins, (2) adding grain and yeast to the pulverized substances to undergo fermentation, (3) heating the fermented products, (4) pulverizing the heated product, (5) adding a Lactobacillaceae culture or a *Bacillus subtilis* culture to the pulverized products obtained from Stage (4) and fermenting the culture under aerobic conditions as described in my Japanese Unexamined Patent Publication No. 5-244962. Also, such an organism active agent can be obtained from Orient Green Co., Ltd. under the trade name of Vitaly Aminon.

(Aerobic Microorganisms)

In the present invention, a source of aerobic microorganisms and an essence of Basidiomycetes are incorporated into the above-mentioned organic active agent to initiate the culturing. In this case, the term "aerobic microorganisms" intended herein means all aerobic microorganisms existing in soil. Typical examples of aerobic microorganisms include, but are not restricted to, those generally existing in nature such as Bacillus, Pseudomonas, Cytophaga, Cellulpmonas belonging to gram-negative aerobic microorganisms, aerobic spore bacteria, and gliding true bacteria, and the present invention is not restricted thereto as long as they do not inhibit the effects of the present invention. The most popularized source of the aerobic microorganisms include humus obtained by converting leaves of broadleaf trees etc. into humus in nature, and preference is given to the use of humus whose conversion is in progress. With regard to the amount of the source for the aerobic microorganisms incorporated into the organism active agent, humus is generally incorporated in an amount of from 1 to 7% by weight, and preferably from 2 to 6% by weight, based on 1 ton of the organism active agent. If the amount is less than 2% by weight, the culture progresses slowly. Conversely, if the amount exceeds the upper limit, the resulting culture thickens, resulting in bad ventilation of air, and causing spots in the culture.

(Basidiomycetes)

As the Basidinomycetes incorporated together with the aerobic microorganisms, *Pleurotus coruncopiae*, preferably new mushroom (called *Pleurotus N*) described in my Japanese Unexamined Patent Publication No. 5-252842 are used as essential components. Other Basidinomycetes can be incorporated as long as they do not impair the effects and the functions of the present invention. It is usual to incorporate such Basidinomycetes as an essence. The amount of the Basidinomycetes incorporated is freely selected depending upon the situation, like the amount of the aerobic microorganisms, and preferably the essence is incorporated in an amount of 1 to 7 liters, more preferably from 1 to 5 liters, per ton of the organism active agent. The incorporation of such specific Basidinomycetes extremely enhances the productivity of cellulase.

(Aerobic Culturing of Aerobic Microorganisms and Basidinomycetes)

The aerobic microorganisms and the Basidinomycetes are incorporated in the organism active agent under aerobic conditions, i.e., under aeration, at normal temperature and normal pressure, for 2 to 5 weeks, preferably from 20 to 30 days, to carry out their culturing. When the culturing is completed, the culture which has bad smells is deodorized (hereinafter this culture is referred to as "OM mother liquid"). The OM mother liquid is a culture containing the aerobic microorganisms, Basidinomycetes, and their metabolites.

(Anaerobic Microorganisms)

Consequently, anaerobic microorganisms are incorporated in the OM mother liquid thus prepared to continue the culturing. The anaerobic microorganisms incorporated at this time essentially contain bacteria belonging to gram true bacteria and gram positive fermentative bacteria. As a source for such anaerobic bacteria, a sludge from sewage can be mentioned. The amount of the source of the anaerobic bacteria incorporated in the organism active agent is from 1 to 7% by weight, preferably from 2 to 6% by weight, based on one ton of the OM mother liquid. If the amount is less than the above range, the culturing proceeds too slowly. Conversely, if it exceeds the above range, the consistency, for example, caused by the sludge substances, is increased, which will become a factor for preventing a progress in the next stage. After the source for the anaerobic bacteria is incorporated in the OM mother liquid, the culturing is continued under anaerobic conditions, i.e., left standing without aeration, usually at normal temperature and at normal pressure for two to five weeks, preferably from 20 to 30 days. When the culturing is continued as described above, the odor originating from the source disappears to obtain odorless OM liquid. In addition to the above components, the microorganisms and their metabolites are contained in this OM liquid.

(Photosynthetic Bacteria: Option)

Optionally, at the same time with the culturing of the anaerobic bacteria, during the culturing or after culturing, photosynthetic bacteria may be added to continue the culturing under dark anaerobic conditions. Examples of the photosynthetic bacteria include cyanobacteria, green sulfur bacteria, green non-sulfur bacteria, and purple sulfur bacteria, the culturing together with these photosynthetic bacteria increases the reducing power. The amount of these optional photosynthetic bacteria is from 1 to 10 liters, preferably from 2 to 5 liters, per one ton of the OM liquid.

To the OM liquid thus obtained, carbonaceous substances originating from plants are added and the culturing is continued under anaerobic conditions for approximately 3 to 10 weeks to produce OME mother liquid in which carbon decomposing catalyst is produced.

By diluting the OME mother liquid thus obtained with the OM liquid in an amount approximately 2 to 4 times the OME mother liquid, OME culture (hereinafter referred to as "OME") is obtained.

OME may also be diluted with water preferably from 300 to 5000 times, and more preferably from 500 to 3000 times its own volume (hereinafter referred to as "OME diluent").

Also, OME can be absorbed in a carrier as described herein below.

(DCP: OME-containing Powdery Carrier)

According to the second aspect of the present invention, an OME components-containing carrier (hereinafter referred to as "DCP")obtained by treating finely pulverized carbonaceous substances with OME or OME diluent to dissolve the carbon is provided.

As one characteristic of OME, OME contains an enzyme which dissolves carbon as described above. Specifically, when finely pulverized carbonaceous substances are treated with OME (an undiluted or diluted solution diluted with an aqueous medium), the carbonaceous substances are dissolved by the action of the carbon decomposing catalyst contained in the OM active components, to absorb OME active components (enzymes and microorganisms) in the dissolved carbonaceous substances, to thereby obtain a carrier containing OME active components, which carries out special functions.

The finely pulverized carbonaceous substances used in the production of DCP mean fine powders of graphite carbon and amorphous carbon. Generally, they are obtained by burning a carbon source at a low temperature, preferably at a temperature of not more than approximately 400 C. The origin is not specifically restricted as long as the objects of the present invention can be attained.

As the carbon source for DCP, cellulose carbons such as from woods, pulverized products thereof, wood shavings, chips, plants, plant carbons originating from plants containing hydrocarbon, protein type carbons originating from plants and animals containing proteins, and petroleum carbons from petroleum can be mentioned. They can be used alone or as a mixture of two or more thereof. Preference is given to use carbons originating from various sources, which are discharged as garbage.

When the carbonaceous substances and OME (or diluent thereof) are mixed with stirring, the proportion of the carbonaceous substances to OME is not restricted as long as it does not impair the objects and effects of the present invention. Also, with regard to the method of mixing them, it is possible to introduce the microorganism culture into the carbonaceous substances or to introduce the carbonaceous substances into the microorganism culture. Preference is given to the mixing of the finely pulverized carbonaceous substances with an aqueous solution containing the microorganisms with stirring.

When the finely pulverized carbonaceous substances are mixed with an aqueous solution containing the microorganisms with stirring, the carbonaceous substances gradually decompose. When the stirring is continued for 1 to 4 weeks, the carbonaceous substances are in the form of a cake or sludge in which the carbonaceous substances come to be in a syrupy state, in which case the load of the stirring is moderated.

The cake carrier or the sludge carrier can be used as it is, and it is also possible to utilize it as a sludge carrier having a desired water content by exposing the wet carrier to the sun or spontaneously drying the wet carrier. Also, the OME carrier can be used as a fine powder.

(RCS: Porous Absorbing Material)

The third aspect of the present invention relates to a porous absorbing material containing active components of OME in the pores thereof (hereinafter referred to as "RCS") by impregnating a porous absorbing material with OME or OME diluent.

Porous absorbing materials in RCS may not be specifically restricted as long as the active components of OME can be introduced into the pores, and examples include active charcoal, SOG sands, porous minerals such as tourmaline, various ceramics, and preferably active charcoal. The shape of the porous absorbing material used in the present invention is also not specifically restricted, and the porous absorbing material may be in a granular form, a fibrous form, or a shaped form. The granular form is particularly preferable.

The porosity of the porous absorbing material used in the present invention is also not specifically restricted as long as it is possible to inhabit the microorganisms of OME in the pores as the habitat and absorb the enzymes of OME to introduce active components into the pores.

When the used porous absorbing material is impregnated with OME or OME diluent, the recovery of the used absorbing material can be carried out at the same time.

Although the conditions for impregnation of the porous absorbing material with OME or OME diluent are not specifically restricted, the porous absorbing material having been washed with water may be impregnated usually for at least 8 hours, preferably for at least 24 hours, at normal temperature and normal pressure, with or without aeration. In the case of utilizing the used porous absorbing material, it is preferably impregnated for from 24 to 72 hours. When the activated carbon is utilized as the porous absorbing material, impregnation for a period exceeding 72 hours is not preferable, because the carbon is dissolved.

Characteristics of OM/OME/DCP/RCS

1. OM cultured in the present invention contains OM active components, i.e., aerobic bacteria, anaerobic bacteria, specific Basidiomycetes, photosynthetic bacteria, as well as enzymes which are metabolites thereof.

Surprisingly, aerobic bacteria can live in symbiosis with anaerobic bacteria in our culture, which is impossible in the prior art. What is more, OM containing such bacteria and enzymes has the following unique characteristics through the synergism thereof. In addition to the characteristics of OM, OME has the feature of decomposing carbon. It is assumed that OME contains carbon-decomposing enzymes. For this reason, OME can be used as the unique carrier (DCP) and the unique absorbing material (RCS).

2. Due to the actions of enzymes and bacteria, OM, OME, and OME-alpha selectively cause the following reactions with target substances.

I. Hydrolysis

  a.

  b.

  c.

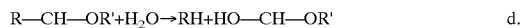  d.

(where R and R' are independently a hydrocarbon group, which may be substituted)

II. Cleavage

  a.

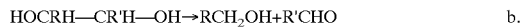  b.

(where R and R' are independently a hydrocarbon group, which may be substituted)

III. Oxidation/Reduction

  a.

  b.

IV. Dehydrogenation

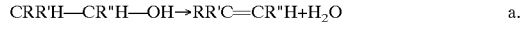  a.

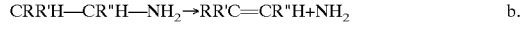  b.

(where R, R' and R" are independently a hydrocarbon group, which may be substituted)

V. Dehydrohaloganation

  a.

(where R is a hydrocarbon group which may be substituted, and X is a halogen)

VI. Substitution

  a.

  b.

(where R is a hydrocarbon group which may be substituted, and X is a halogen)

Eliminating phenolic OH and halogen bonded to aromatic ring:

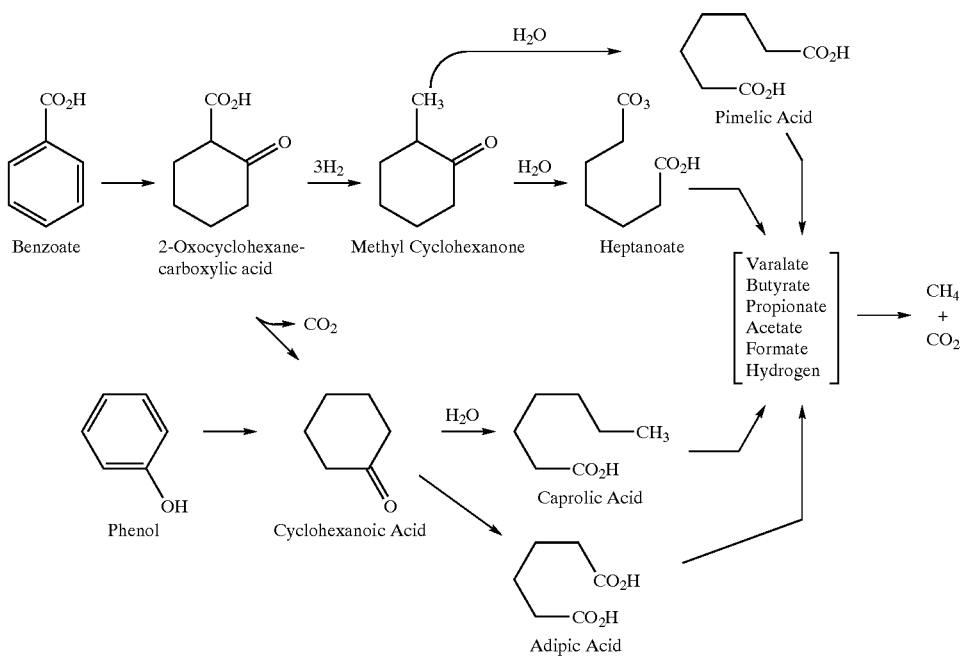

4. Decomposition of Hard-to-Decompose Substances

Sawdust and bark, etc. of needle-leaf trees contain phenols, tannin, essential oils, and other substances which inhibit the growth of plants. Phenolic acids, non-phenolic acids, and high fatty acids in green sawdust inhibit the growth of seed roots and side roots. Particularly, the ligneous substances of ligneous sawdust have an extremely high C/N ratio of from 100 to 1,500, and they are hardly decomposed due to the tight bond between cellulose and lignin. Such vegetable residue can be gradually decomposed by means of continuous co-metabolism of gliding genuine bacteria, myxo cytes, acthinomycetes, filamentous fungi, and the like in OM, OME, and OME-alpha. OM, OME, and OME-alpha serve as co-substrate substances for symbiosis biological active substances.

5. Removal of Heavy Metals

OME has functions for removing heavy metals such as zinc, lead, tin, nickel, chromium, copper, cobalt, manganese, mercury, cadmium, and dross in semiconductor liquids. Although the mechanism for removing heavy metals by OME is unclear, such functions have been found on the basis of experiments of my treatments of exhaust liquids from plating and semiconductor production.

6. Decomposition of Organic Substances (Conversion of Harmful Organic Substances into Harmless Substances, Decoloration and Deodorization)

Due to the function of decomposing halogens possessed by OME, organic halogen compounds, e.g., halogenated aromatic compounds such as dioxins, polychlorobiphenyls, and chlorobenzene; and halogenated aliphatic compounds such as tetrachloroethylene, trichloroethylene, dichloromethane, carbon tetrachloride, 1,2-dichloroethylene, 1,1-dichloroethylene, cis-1,2-dichloroethylene, 1,1,1-trichloroethane, 1,1,2-trichloroethane, and 1,3-dichloropropene can be decomposed. Also, dyestuffs such as azo dyestuffs, as well as odorous substances such as methylmercaptan, captans, indoles, and statoles can be decomposed.

7. Decomposition of Inorganic Substances

Reduction of Nitrogen

Anaerobic or facultative anaerobic chemical synthesis-dependent nutrition bacteria (chemoheterotrophs) contained in OM and OME have either or both functions of anaerobic breath and fermentation. The anaerobic breath has substantially the same biochemical route as that of aerobic metabolism (aerobic breath), and the final electron-receptor of the electron-transmitting chain is nitrate ($NO^{3-}$), sulfate ($SO_4^{3-}$), fumaric acid or trimethylamine oxide instead of oxygen. In the case of $NO^{3-}$ or $SO_4^{3-}$, the reduced products also act as the final electron-receptors.

In reducing $NO^{3-}$, $NO^{3-}$ is reduced into $NO^{2-}$ through denitrifying bacteria, and further into $N_2O$ and finally converted into $N_2$ gas as the final product. Typical bacteria having the denitrifying function contained in OME include Rohodobacter, Cyanobacteria, Cytophaga, etc.

Decomposition of Ammonia

Ammonia is decomposed in the presence of OME according to the following reactions:

$$2NH_3 + H_2O \rightarrow (NH_4)_2CO_3$$

$$2(NH_4OH) + H_2O + CO_2 \rightarrow (NH_4)_2CO_3 + 2H_2O$$

Decomposition of Hydrogen Sulfide

Hydrogen sulfide is reacted with oxygen under an aerobic condition to become water and sulfur which are harmless, and the sulfur is further oxidized into sulfur ions.

$$2H_2S + O_2 \rightarrow 2H_2O + 2S$$

Decomposition of Methyl Mercaptan ($CH_3SH$)

Methyl mercaptan becomes methyl alcohol and sulfur via a two-stage oxidation, and further becomes carbon dioxide and water.

$$2CH_3SH + O_2 \rightarrow 2CH_3OH + 2S$$

$$2CH_3OH + O_2 \rightarrow 2CO_2 + H_2O$$

8. Desalting

As a result of our repeated experiments, OME has been confirmed to substantially decompose sodium chloride (see Example below).

9. Removal of Water Bloom

When OME is sprayed onto algae or water bloom generated due to enrichment, water bloom can instantly be decomposed and removed.

10. Prevention of Diseases in Plants

When OME is applied to a plant which has been affected with stem canker, clubroot, ring spot, target spot, brown canker, powdery mildew, rust, or any other diseases-causing germs, particularly to the root of the plant and rhizosphere of the plant to wash the affected portion, this changes the state of the plant into reduced conditions to stop the growth of the disease causing germs. In addition, due to the actions of the gliding Eubacteria and of Basidiomycetes contained in OME, these germs undergo hydrolysis, and are removed thereby.

11. Aggregation of Seston

DCP has a function of aggregating seston regardless of the kinds of seston.

12. Decomposition of Polluted Sediment and Sludge

DCP has a function of decomposing the polluted sediments and sludge deposited on the bottom of the water. Although the reaction mechanisms for decomposing the polluted sediments and sludge are not clear, this function has been repeatedly confirmed by actual applications. To be specific, the polluted sediments and sludge deposited on the bottom of the water are decomposed about 2 weeks to 1 month after the application of DCP.

13. Applicability in All pH Ranges and Neutralization

OME functions over all pH ranges. Also, OME has a function of changing the pH to neutral (see Example below). According to my experiments, from very strong acidic condition in the case of treating exhaust water from the production of pickled plum to strong alkaline conditions having pH level over 14, such as treatment of NaOH, OME exhibits its functions and turns the pH level toward neutral.

14. Decrease in BOD/COD

OME can decrease BOD/COD.

15. Harmlessness

According to acute toxic testing utilizing mice, OME has been proven to be harmless (see Example 1 below)

Application of OME/DCP/RCS

OME, DCP, and DCP having the unique characteristics as described above can be applied as follows:

A: Application to Agricultural Fields

OME, OME enzymes, OME diluent, DCP and RCS can be applied to various fields among the agricultural fields. Typical applications are summarized in the following Table 1.

TABLE 1

Application of OME/DCP/RCS (1): Application to Agricultural Fields

| | Techniques to be applied | Application | Contents |
|---|---|---|---|
| 1 | Soil Conversion material, Activation of Crumb structure, Fertilization of Exhaust Soil, Desert Seashore soil, etc. | OME 1) Physical pulverization, and then decomposition of Cellulose and Lignin by OME | Sawdust of needle leaf trees, thinned out trees, fallen trees, buckwheat chaff, and primarily treated exhaust material from construction are utilized as soil base material. The soil base material is spread over exhaust soil, desert, seashore, etc, on which OME is sprayed, and a small amount of chicken droppings is added. |
| 2 | Prevention from disease in plants | OME | Treatment of a plant system with OME diluent |
| 3 | Prevention of microorganisms attack against plants/revival from damping off | OME | Treatment of a plant system with OME diluent |
| 4 | Composting feces and urine of livestock, including pigs, and poultry | OME/DCP | OME diluent and/or DCP is (are) added to feces and urine originating from livestock. |
| 5 | Provision of soil base material without agricultural chemicals or chemical fertilizers | OM/OME | Sawdust, an exhaust medium from the cultivation of mushrooms made of needle leaf trees, garbage, or weeds are hydrolyzed by OME, and the decomposed liquid is used as a liquid fertilizer. |

(A-1: OME Soil Base Material)

The term "soil base material" used in this embodiment means a cellulose substance that can be applied to a soil to revive the crumb structure of the soil and whose cellulose is decomposed by OME or OME diluent to become soil. Examples of such cellulose substances include sawdust, dried leaves, bark, husks (e.g., chaff, buckwheat chaff), cut straw, primarily treated exhaust wood from construction, fallen wood, and the like, and they can be used singly or as a mixture of two or more thereof. In terms of ready availability and inexpensive cost, sawdust, particularly sawdust of needle leaf trees, which has been difficult to decompose, is preferable. In the case of utilizing relatively large materials such as exhaust wood from construction and fallen wood, they can be used after pulverization into appropriate pieces.

In this embodiment, the soil base material is applied to the soil to be treated, the soil applicable in this embodiment including normal soils, soils exhausted by the application of agricultural chemicals, dormant soil in crop rotation, acidified soil due to acidic rain etc., desertified soils, sandy soils around rivers, seashore deserts and beaches containing salts.

The amount of the soil base material to be spread depends upon the types of soils to be treated, climates, plants to be cultivated, and generally a depth of from 1 cm to 100 cm, preferably from 2 cm to 50 cm, is used.

Subsequently, OME, preferably OME whose productivity of cellulase is enhanced, is sprayed onto the soil where the soil base material has been spread over.

According to my experiments, even if the conventional culture composed of anaerobic bacteria and aerobic bacteria living together with each other and having an ability to decompose cellulose is utilized, the effect of the present invention cannot be obtained. In contrast, although the difference cannot be recognized, it comes as a surprise that the culture utilizing the specific Basidiomvcotina at the same time can obtain the objective effect for the first time.

Although OME can be utilized as an undiluted solution, it is usually diluted with water by 500 to 2,000 times, preferably approximately 1,000 times. In the present invention, OME diluent may be sprayed on the dried soil until it is in a perfectly wet state.

When the soil base material of the present invention is applied to the soil to be treated and when OME, preferably OME whose cellulase productivity has been enhanced, is sprayed on the material, and the soil is left standing for at least several days, preferably at least one month, more preferably at least two months, the soil is improved to be able to cultivate plants. In the case where improvement in the soil proceeds slowly, additional OME may be sprayed thereon. The spraying may be repeated once to three times as occasion demands. In this case, by mixing sewage sludge or feces and urine of livestock with the soil base material, and turning the soil upside-down once to three times per month, a very good organic soil can be obtained.

These soil base materials have a first feature of being able to perfectly decompose harmful substances, for example contained in fibrous materials or garbage to be treated. For example, when OME diluent is sprayed onto fallen leaves of fruits and straw which have been sprayed with any agricultural chemicals, and fibrous material from plants which have been cultivated utilizing feces and urine of livestock having been bred with the injection of antibiotics etc as fertilizer, the harmful substances can be converted into harmless ones. The second feature of this embodiment resides in that in addition to the usual soil, OME diluent may be applied to soil exhausted due to the application of agricultural chemicals, dormant soil in crop rotation, acidified soil due to acidic rain etc., desertified soils, sandy soils around rivers, and seashore deserts or beaches containing salts to convert these soils into good soils capable of cultivating crops in a good manner.

By the use of the soil base material, the soil is converted into a reduced type soil, which can produce crops and fruits, etc., while preventing insects and disease causing germs.

It has been particularly surprising that various crops can be cultivated even on sandy soil containing salts, i.e., seashores and beaches.

Whereas OME diluent is sprayed on cellulose substances originating from plants as the soil base material previously spread over the soil in one embodiment, the cellulose substances may be previously admixed with OME to be ready for use in another embodiment.

A-2 Suppression of Insects and Disease Causing Germs

A process for optimizing a plant system composed of a container for cultivating plants (planter), a solid medium for cultivating plants, and (a) plant(s) is provided. Specifically, the system is incorporated into a sealable container, which is then filled with OME or OME diluent, and the container is sealed. When the system is held in the sealable container for a period sufficient for killing the insects and eggs thereof existing in the medium or on the plant(s), the insects and their eggs can be suppressed.

It is also possible that OME treats non-healthy plants, i.e., withering plants. In the preferred embodiment, the sealable container is transparent, and the plants in the sealable container are held while being exposed to the sunshine.

Similarly, OME can also treat a solid medium for plants or mushrooms. Specifically, the medium is impregnated in OME or OME diluent for a period sufficient for killing insects and their eggs contained in the medium.

Suppression of insects causing damage to plants by using OME or OME diluent will now be described by referring to the drawing.

FIG. 1 is a cross-sectional view illustrating an inventive process for optimizing a plant system composed of a container for cultivating plants, a medium for cultivating plants, and a plant to be cultivated.

As shown in FIG. 1, in the suppression of insects according to this embodiment, a plant system S composed of a container 1 for cultivating plants (pot 1), a medium 2 for cultivating plants, and a potted plant 3 is incorporated in a sealable container 4. The plant system S applicable in the present invention is not specifically restricted, and all potted plants 3 which are cultivated in the medium 2 contained in the pot 1 are applicable. Typical examples of plants applicable to the present invention include, but are not restricted to, trees such as pine and plum; various annual and perennial plants; various herbs, edible plants such as potatoes, tomatoes, parsley, and eggplants. The medium for cultivating plants include, for example, black soil, humus obtained by decaying fallen leaves, and the like. Usually, an optimal medium is selected corresponding to the plant 3 to be cultivated. Various pots 1 can be used for cultivating the plant 3 in the present invention, and examples include flowerpots, planters made of ceramics or wood, etc.

Such a plant system S is incorporated into the sealable container in the present invention. The material and shape of the sealable container are not specifically restricted as long as the plant system can be perfectly inserted and then sealed, and no liquid leaks out after filling with the culture or the diluent. A plastic-made container or a bag can be utilized. From the viewpoint of being capable of having exposure to sunshine after being filled with the culture or its diluent, and to observe the situations of the plant system, at least part of, preferably the whole of, the sealable container is transparent. One plant system S is inserted in the container, but if there is room, two or more systems S may also be inserted.

In this embodiment, the sealable container 4 is filled with OME or OME diluent 5.

OME (diluent) 5 possesses the capability to kill the insects and eggs thereof causing damage to plants, to decompose chemical substances such as agricultural chemicals, and to improve the medium such as soil. If the plant system S is impregnated in usual water or the culture described in Japanese Examined Patent Publication No. 4-42355, the root of the plant is rotted, but in the case of using OME 5, surprisingly no root is found to be rotted.

After the container 4 containing the plant system S is filled with OME (diluent) 5 as described above, the container is sealed and left standing for a prescribed period. The treatment time is a period sufficient for killing the insects and their eggs contained in the medium and depends upon type of the plant, the type of the medium, and the conditions for generating the insects causing damage to plants. Usually, it is held for from several minutes to several hours, e.g., from 2 minutes to 10 hours. By the impregnation of the plant system S in OME (diluent) 5 as described above, the insects and their eggs are killed and, at the same time, the medium is activated.

The operation may be carried out once, but two or more operations can also be carried out at several day intervals. In the case where withering of the plant 3 proceeds, the plant can be activated and revived by this treatment. The solid medium 2 can be repeatedly utilized after the lifetime of the plant is ended by the treatment described above.

In this embodiment, in addition to the plant system, the medium itself, such as the medium for cultivating plants or mushrooms, is treated with OME to carry out the suppression of the insects. Since how to treat the medium is the same as how to treat the plant system except for there being no requirement of the sealable container and a much longer time being required to carry out the treatment in order to perfectly activate the medium due to there being no plant, repeated description is omitted. In the case of the medium for cultivating mushrooms, ticks and other harmful insects spread over the medium can be removed and the treated medium can be repeatedly used.

The treatment described above can kill the insects and their eggs contained in the medium, to suppress their breeding and, at the same time, continue the suppression effect over a prolong period of time. Also, by this treatment, the solid medium can be repeatedly used.

A-3 Suppression of Pathogenic Organisms in Plant System

Similarly, portions of roots of the plant and the soil can be washed with OME to revive a plant attacked by various pathogenic microorganisms such as root rot and stem canker, sometimes even in the situation where rotting is in progress.

In this embodiment, a plant attacked by photogenic microorganisms such as stem canker, root nodule, root rot, brown canker, powdery mildew, and rust can be revived, particularly by spraying OM or OME to the root atmosphere of the plant, and washing the root atmosphere with OM or OME to convert the root atmosphere, which has become acidic and in a hard state, into a soft and reduced state. This makes it possible to prevent the spread of the photogenic microorganisms. The photogenic microorganisms are killed due to the attack of the Basidoimycetes, which is one of the active components of OME, and then hydrolyzed by the hydrolytic enzyme contained in OME.

Specifically, the whole of the plant infected with these photogenic microorganisms is impregnated in OME diluent. This revives the plant.

In the case of the plant attacked by stem canker, the infected portions are shaved off, DCP slurry is preferably applied to the shaved portions, dried to cover the shaved portions with dried DCP.

A-4 Composting of Feces and Urine Originating from Livestock and Poultry

When OME diluent or DCP is added to the feces and urine of livestock, these feces and urine are deodorized and converted into excellent compost. Ideal compost can be obtained by mixing and stirring the resulting compost with the sawdust of needle leaf trees.

B. Application to Environmental Fields (Including Conversion of Seawater into Freshwater)

In addition to the applications to the agricultural fields, OME, OME diluent, DCP and RCS are applicable to various applications in the environmental fields.

Examples of Applications to Environments based on OME active components are listed in the following Table 2.

TABLE 2

Application (2) of OME/DCP/RCS
Application to Environmental Field
(Application to Solids)

| | Application Technique | Application | Contents |
|---|---|---|---|
| 1 | Production and recovery of porous absorbing materials | OME | Similar to the production of RCS Immersion of Absorbing Material in OME |
| 2 | Garbage treatment | OME | Garbage decomposing material produced by adding a cellulose substance similar to that of the soil base material to OME |
| 3 | Treatment of sands, particularly salty sands | DCP | Addition of DCP; and washing with water, etc. to remove salts and harmful substances from salty sands, etc. |
| 4 | Treatment of burned ash and fly Ash | DCP | Addition of DCP and washing with water, etc. |

B-1) Production and Recovery of Porous Absorbing Material

With regard to the production of the recovery of porous absorbing material, the details are omitted because the description has been made in the column of RCS, including the recovery of used absorbing material.

B-2) Treatment of Garbage

In this embodiment, a garbage treating material (garbage decomposing material) produced on the basis of OME is used to treat garbage.

(Cellulose Substances Originating from Plants)

The garbage treating material according to the present invention is based on the cellulose substances originating from plants. Examples of the cellulose substances originating from plants are those described in the soil base material described in Column A-1 above and an exhaust medium for cultivating mushrooms. It is preferable to add hard-to-decompose substances such as chaff to the cellulose substances, preferably in a proportion of approximately 1 to 0.3–1, in order to obtain good ventilation.

When OME or OME diluent is applied to the cellulose substances originating from the plants described above, aerobic bacteria and anaerobic bacteria live in symbiosis with each other in the cellulose substances as their habitant. In the present invention, such a system is referred to as the "garbage treating material (garbage decomposing material)."

(Process for Treating Garbage)

When the garbage treating material thus produced is allowed to come in contact with garbage, hydraulic enzymes and microorganisms contained in OME described above decompose and ferment the garbage and, at the same time, bad smells contained in the garbage are deodorized with perfectly decomposed sulfur oxides and nitrogen oxides which are sources of bad smells.

In the process for treating the garbage according to this embodiment, garbage can merely be incorporated in a place on which the garbage treating material is placed and then stirred to treat the garbage in an odorless state. Conversely, it is also possible to further place the cellulose substances originating from the plants on the garbage, and to further spray OME liquid onto the cellulose substances. Alternatively, it is possible to directly place the garbage treating material according to this embodiment on the garbage. Particularly, if the cellulose substances are placed on the garbage and then OME liquid is sprayed thereon or the garbage treating material of the present invention is directly placed on the garbage, bad smells are preferably removed in the treatment of the garbage.

Also, it is preferable to intermittently stir the mixture of the material and the garbage twice or three times per day, each time for a period of from 5 to 10 minutes. This treatment can be carried out in an open system or in a sealed container, and the selection may be desirably made. Of course, it is also possible to use the garbage treating material of this embodiment instead of the existing material for the composter or compo-planter. Also, it is preferable that the lower portion of the container is divided by a porous plate, and an outlet for discharging the decomposed liquid is provided on the container. Greater preference is given to the use of a container equipped with means for stirring.

Consequently, the process for treating the garbage according to this embodiment may be carried out in the existing composter or compo-planter. For example, it is also possible that the garbage treating material according to the present invention is applied to a landfill to treat the garbage in situ. This treatment makes it possible to treat the garbage without generating any bad smell.

Depending upon the components in the garbage, when the garbage incorporated in the garbage treating material of this embodiment is left standing for several hours, the decomposition of the garbage is started immediately after the incorporation, and the garbage is completely turned into liquid approximately 24–36 hours after the incorporation.

According this embodiment, the following outstanding effects can be obtained as described above.

1) The garbage treating material according to this embodiment can be produced in a simple manner where the cellulose substances originating from plants are impregnated in OME or OME diluent.
2) The garbage treating material can also be utilized as the garbage decomposing material for the existing compositer, compo-planter, and garbage decomposer as is.
3) When the resulting material for treating the garbage is allowed to come in contact with the garbage, the garbage can be decomposed into a liquid without generation of any bad smell, making it possible to treat the garbage in an inexpensive and simple manner.
4) The resulting liquid can be utilized as a good, odorless liquid fertilizer.

B-3 and 4 Solid Treatment With DCP

DCP can be mixed with and stirred together with sands containing at least one component to be removed, selected from the group consisting of salts, organic harmful substances and heavy metals, to substantially remove the component(s) to be removed.

The term "sands containing at least one component to be removed, selected from the group consisting of salts, organic harmful substances and heavy metals" used in this embodiment means sands containing salts such as sea sands and/or sands containing heavy metals such as zinc, cadmium, and nickel; and/or harmful substances such as aromatic halogen compounds (e.g., PCBs and dioxins); aliphatic halogen compounds (e.g., dichloromethane, trichloromethane, carbon tetrachloride), and azo compounds. The term "substantially remove" means the removal at a level not higher than the level decided in administrative guidance according to a local self-governing body.

This treatment allows for the substantial removal of the salts and harmful substances from the sands containing them. When the resulting mixture comprising the treated sands and DCP is partially or entirely utilized as fine aggregations for construction material such as concrete, a reduced type construction body excelling in purification of water can be obtained.

DCP is mixed and stirred with burned ash to substantially remove the harmful substances contained in the burned ash.

The treatment as described above can substantially remove heavy metals such as lead and zinc and harmful substances such as organic halogen compounds contained in the burned ash, and the treated burned ash can be reused as fine aggregate for construction materials such as concrete. In this case, a resulting construction material of a reduced type and excelling in purification of water can be obtained.

DCP is mixed with and stirred together with exhaust glass containing at least one substance to be removed selected from the group consisting of salts, organic harmful substances, and heavy metals or exhaust glass discharged in the process of the glass production to substantially remove the substances to be removed.

When exhaust glasses, such as soda-lime glass or a by-product cake mainly composed of calcium carbonate discharged from a plant for producing calcined soda in the glass production, is treated with DCP, as described above, sodium chloride, lead, soda ash, and the like can be removed from the glass, etc., which can then be used as a rough aggregate such as slug or a fine aggregate through the pulverization.

B-3 Sands Containing Salts

In this embodiment, DCP can be utilized to carry out the treatment of and mixing with sands containing salts, burned ash, river sands, etc. to be used as a fine aggregation mixture comprising DCP and sands, etc.

If the sand containing salts is treated, at least 1 kg, preferably from 1 to 4 kg, of DCP is mixed per ton of the sands. When the sands containing salts are mixed and stirred with DCP, salts such as sodium chloride are removed from the sands. If the amount of DCP is less than the above range, the removal of salts becomes insufficient. The reason why no upper limit of DCP is set is that the amount of DCP can freely be selected depending upon the requirements of the application, such as in the case of the application to fine aggregation, e.g., for the production of a strongly reduced type of construction material, and in the case of requiring only removal of salts. Generally, it is enough to utilize 2 to 5 kg of DCP per ton of sands. The mixing and stirring may be carried out in a dry state, but it is preferable to add water to the sands to be in the state of slurry. For example, a usual kneader or mixer, or an apparatus marketed under the trade name of MD Cyclone from Daiki Rubber Co. Ltd. may be used to mix and stir the slurry of DCP and sands which are to have substances removed.

Sands Containing Harmful Substances

In this embodiment, it is possible to treat river or sea sands containing harmful substances with DCP. The harmful substances which can be removed in this embodiment include heavy metals such as zinc, lead, chromium, and cadmium; and chemical hazards such as organic halogen compounds (e.g., aromatic halogen compounds such as PCBs, dioxins, and chlorophenols; mono- or poly-halogenated aliphatic compounds), and the like. In this case, the amount of DCP is suitably selected depending upon the kinds and concentration of the harmful substances, and usually the amount is similar to that in the case of the treatment of the sands containing salts.

It is also the subject matter of this embodiment to treat river sands containing a small amount of salts or harmful substances.

Specifically, this embodiment encompasses all the mixtures of sands with DCP, which can be utilized as fine aggregations for producing an excellent reduced type construction material, described later on.

B-4 Burned Ash

In this embodiment, DCP can also be utilized to treat burned ashes similar to the sands containing salts or harmful substances. The term "burned ash" used herein means all burned ash including fly ash. This burned ash sometimes contain metals, such as lead, zinc chromium, mercury, or some other heavy metals, or chemical hazards, such as dioxins and PCBs. The amount of DCP used in the treatment of the burned ash depends upon the types and amounts of the harmful substances contained. However, DCP is generally used in an amount of from approximately 1 to 5 kg per ton of the burned ash. The treatment makes it possible to absorb the metals such as zinc, lead, chromium or some other heavy metals into a stable state and to substantially remove organic halogen compounds such as dioxins and PCB.

In this embodiment, the treated mixture of burned ashes with DCP can be used as a fine aggregation, and also this treatment can be applied as a pretreatment of the usual treatment of the burned ash, such as reclaiming after the removal of the metals by DCP.

Since the pH level of the mixture of the burned ash with DCP is automatically adjusted by the function of the microorganisms and the enzymes contained in DCP, the mixture can be used as a fine aggregation and as reclaiming materials in a safety manner. The treatment of the burned ash may be similar to that of sands. The treatment of the burned ash with DCP may be applied to the treatment of sands. In the case where a higher safety level is required for the construction, the used RCS is again impregnated in the OME liquid for mixing.

(Characteristics of DCP Mixture)

The mixture of DCP with sands or burned ash described above has excellent properties similar to OME, DCP, RCS, etc.

Consequently, when a construction produced from the DCP mixture having the function of the neutralization of pH, and of reducing BOD/COD can be used in a usual drainage ditch or irrigation canal, etc., it can be very useful in terms of purification of sewage. A construction having similar effects can be obtained if DCP is directly added to freshly mixed concrete.

While the embodiments where the sands or burned ash containing salts and harmful substances are treated with DCP and the resulting mixture is mainly used as a fine aggregation have been described, it is also within the scope of the present invention, for example, when part or all of the sands or burned ash containing salts and harmful substances are used as fine aggregations and DCP and usual raw materials for producing concrete are mixed and treated, for example, in a kneader or a concrete mixer for the removal of the harmful substances to be carried out at the same time as the production of freshly mixed concrete. According to this process, there is a merit in having no need for drying the slurrized sands or burned ash.

According to the first embodiment of the present invention as described above, the salts and harmful substances can be substantially removed from the sands or burned ash in a simple manner where DCP is added to and mixed with the sands or burned ash, and the resulting mixture can be utilized as a suitable fine aggregation.

According to another embodiment of the present invention, the harmful substances contained in the burned ash can be removed only in a simple manner where DCP is added to and mixed with the burned ash. The treated burned ash can easily be secondarily treated in the conventional manner or can be directly utilized as a fine aggregation.

The resulting DCP mixture can be utilized as a fine aggregate for producing a reduced type construction material excelling in water purification.

In this embodiment, it is also possible to remove salts and harmful substances and, at the same time to produce freshly mixed concrete for a reduced type construction material. This makes it possible to directly produce without any drying stage at the same time as the treatment.

40. A reduced type construction material obtained from the fine aggregates of claim 39.

2) Application to Liquids

Application to Environmental Fields (Including Conversion of Seawater into Freshwater)

Examples of applications of the present invention to liquids based on the functions of OME active components are listed in the following

TABLE 3

Applications (3) of OME/DCP/RCS: Applied to Environmental Fields
(Applied to Liquids)

| | Applicable Technologies | Application | Method | Contents |
|---|---|---|---|---|
| 6 | Removal of waterbBloom | OME | a | Spraying of OME |
| 7 | Aggregation of seston | DCP | b | Spraying of DCP |
| 8 | Removal of Polluted Sludge | DCP | b | Spraying of DCP |

TABLE 3-continued

Applications (3) of OME/DCP/RCS: Applied to Environmental Fields
(Applied to Liquids)

| | Applicable Technologics | Application | Method | Contents |
|---|---|---|---|---|
| 9 | Treatment of the sea area polluted, e.g., with petroleum | DCP/ RCS | b/c | Spraying of DCP, and passing the liquid though RCS filter |
| 10 | Conversion of Seawater into Freshwater | DCP/ RCS | b/c | Pretreatment with DCP and passing the liquid though RCS filter |
| 11 | Treatment of Exhaust Liquids | DCP/ RCS | b/c | Pretreatment with DCP and passing the liquid though RCS filter. Applicable to treatment of exhaust liquids from chemical industries such as developing photo, semiconductor processing, plating industry; from food processing such as pickling; pigment containing exhaust liquids, etc. to be converted into harmless, deodorized. Also applicable to purification of exhaust liquid from stock breeding, pig breeding, chicken breeding, sewage, etc. |

The treatment of liquids according to the present invention is roughly divided into three processes: (a) a process including spraying OME (e.g., removal of water bloom (Cyano bacteria/Microcystis); (b) a process including spraying DCP; and (c) a process including optional spraying of DCP as a pretreatment and passing the liquid through (a) filter(s) containing RCS.

B-6 Removal of Water Bloom: Process (a)

When OME diluent is sprayed onto the surface of water on which algae (Cyano bacteria/Microcystis), such as water bloom generated due to eutrophication of lakes and marshes are floating, the water bloom etc., is instantly removed.

B-7 Aggregation of Seston: Process (b)

In this embodiment, through the application of DCP to water containing seston, such as organic exhaust water including exhaust water from sewage, exhaust water from food processing, exhaust water of feces and urine from livestock breeding such as pig breeding, eutrophicated lakes and marshes; inorganic exhaust water e.g., from a chemical plant, the seston is aggregated, and the aggregates float on the surface of the water or precipitate at the bottom of the water depending upon their specific gravities. The floating substances and/or the precipitates can be separated, for example, by filtration. In contrast to the conventional macromolecular aggregates or aluminum sulfate, this process does not requires any secondary treatment. In the present invention, irrelevant of whether water is inorganic or organic, various types of sestons can be treated. For example, when several milligrams of DCP is applied to ton of a muddy lake or marsh containing a large amount of sestons and then agitated, the transparency of the water is increased and, the floating substances and the precipitates due to the application of DCP are observed on the upper and the lower layers, respectively.

B-8 Removal of Polluted Sediment: Process (b)

DCP further has a function of decomposing polluted sediment deposited on the bottom. Although the mechanism for decomposing the polluted sediment by means of the microorganisms-containing carrier of the present invention has not yet been understood, when the microorganisms-containing carrier of the present invention is applied to the water having polluted sediment deposited on the bottom thereof, the polluted sediment has been found to be gradually decomposed two weeks or 1 month after the application.

B-9 Treatment of Water Containing Petroleum: Process (b)

DCP can be used to remove heavy oil from petroleum-containing water, particularly from seawater or river water polluted with heavy oil, in a manner similar to the treatment of seston. Specifically, DCP selectively absorbs the heavy oil. The heavy oil absorbed on the carrier of the present invention is decomposed into carbon dioxide and water, which are harmless, due to the function of the active components of OME. With regard to the sulfur contained in the heavy oil, sulfur components such as sulfur dioxide can also be instantly decomposed through the function of sulfur bacteria existing in seawater. Although hydrogen sulfide somewhat occurs due to the interaction of sulfate oxidation bacteria and sulfate reduction bacteria, hydrogen sulfide thus generated can be instantly decomposed into a harmless state by the spraying of OME diluent. Since the active components of OME have a function of decomposing halogens, heavy oil containing them can be decomposed into a harmless state.

B-10 Conversion of Seawater into Freshwater: Process (c)

It is possible to convert seawater into freshwater by (a) incorporating an appropriate amount of DCP into seawater to be treated under forcedly stirring conditions, and forcedly stirring for an appropriate period; and (b) after optionally repeating stage (a) once or several times, passing the seawater through a filter comprising RCS.

(Stage for Treating Seawater with DCP)

As a result of the investigations, it has been found that DCP has a function of removing salts in seawater under specific conditions.

Specifically, according to this embodiment, DCP is mixed and forcibly stirred together with the seawater. The stirring means used in this case is not specifically restricted as long as DCP can be sufficiently in contact with the seawater to carry out the conversion of seawater into freshwater by the function of DCP. Examples include stirring by means of a mixer and stirring by means of a jet water stream. Particularly preference is given to the use of a forcible stirring by means of OHR line mixer produced from Seika Sangyo Co. Ltd. The stage for having DCP to come into contact with seawater with forcible stirring may be carried out once, but it may be repeated several times as required.

The OHR line mixer is a forcible stirrer in which a process of two different fluids each passing through spiral paths collide with each other take place. In the case where this process is applied in the present invention, a fluid A, in which DCP is previously added to a part of seawater is made to come into contact with untreated seawater B to be reacted.

When seawater comes in contact with DCP in this manner, approximately 80% of the salt in the seawater can be removed. Since DCP has a very high performance for removing various harmful substances, the polluted substances, even contained in the seawater, can be advantageously removed.

(Treatment with RCS)

The water from which approximately 80% of the salts are removed is passed through a filter containing RCS. When the seawater treated in the former stage is passed through the filter containing RCS, the seawater is perfectly converted into freshwater. It is also noted that seawater which is not so polluted can be converted into freshwater only by passing it through the RCS filter to remove salts.

B-11 Treatment of Exhaust Liquid

DCP, RCS or a combination of them can be used to purify various kinds of exhaust water containing various harmful substances, exhaust water whose pH level is strongly acidic or strongly alkaline, exhaust water containing metals, bad smelling exhaust water, colored exhaust water, and exhaust water in combination of two or more thereof.

a) Purification of Exhaust Water with DCP

DCP which is a powdery carrier is sprayed to carry out the purification of the exhaust water. DCP is sprayed (1) for purifying exhaust water whose pollution degree is relatively low; (2) for purifying exhaust water which is difficult to be purified by being passed through the RCS filter described later on, such as lakes or marches having a relatively wide area, and rivers; and (3) to carry out a pretreatment for the treatment with the RCS filter which is described later on.

b) Purification of Exhaust Water with RCS

The purification of exhaust water with RCS, in which the exhaust water is passed through a filter or filters containing RCS, is carried out as the final treatment. Exhaust water whose polluted degree is extremely high can be purified by passing the exhaust water through RCS filters several times.

The water purification using DCP, RCS or the combination thereof is carried out in essentially the same manner as in the case of conversion of seawater into freshwater.

Examples of water purification include, but are not restricted to, purification of exhaust water from chemical plants, particularly exhaust water from plating industries, photographic exhaust water, exhaust water containing dyestuffs, exhaust water containing PCBs, dioxins, or any other harmful substances, exhaust water from food processing, such as salted plum exhaust water discharged in the course of producing pickled plums, and the like.

Figure 2:
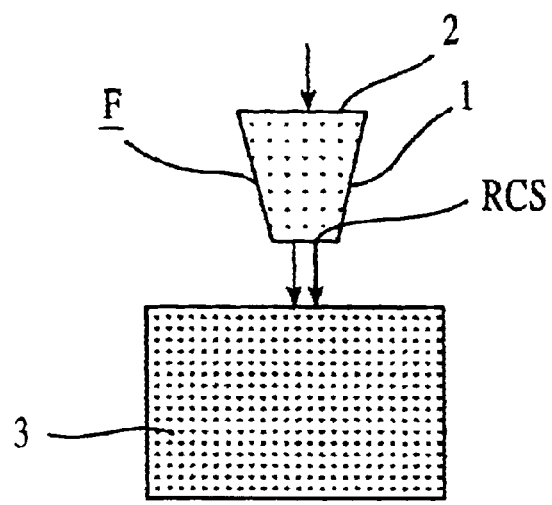
FIGS. 2 and 3 are cross sectional views, each showing an apparatus for treating liquid according to one embodiment of the present invention.
Figure 2:
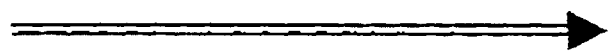
Figure 2:
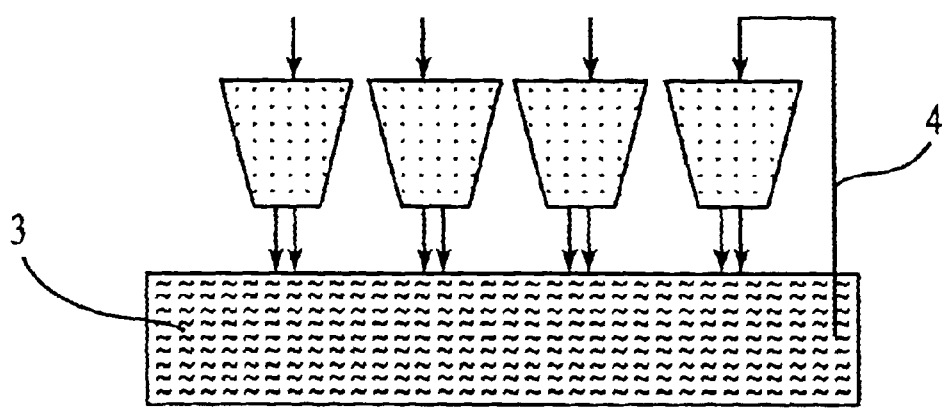
Figure 3:
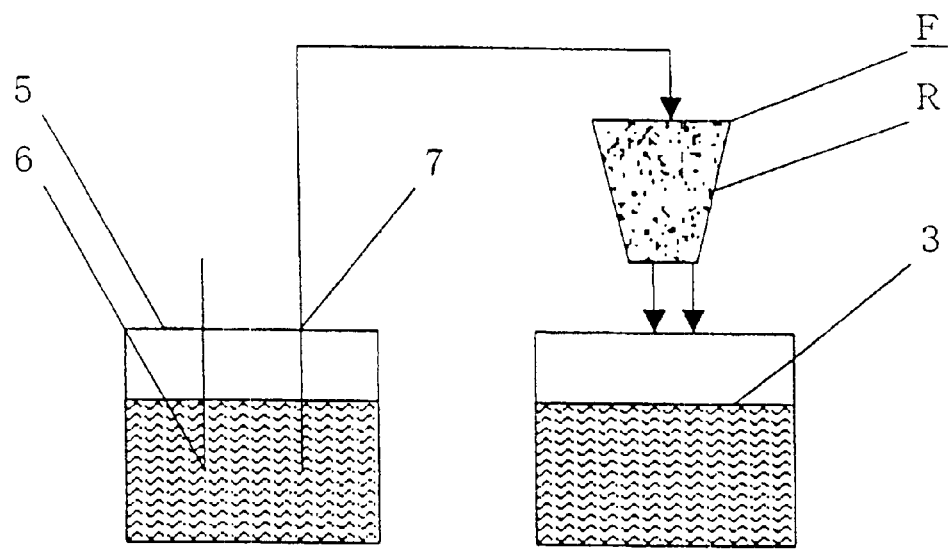
Figure 4:
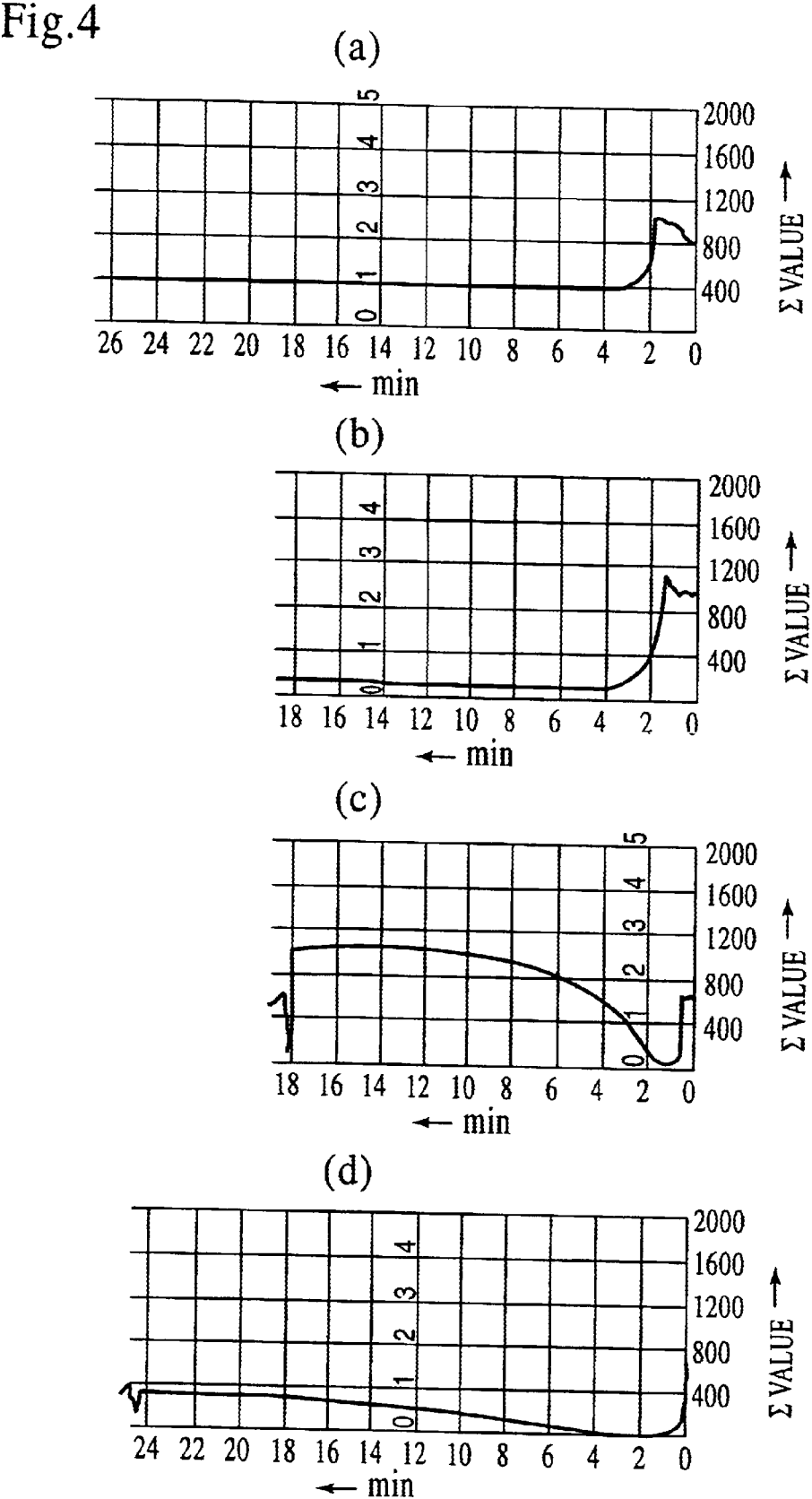

This seawater and harmful substances can be purified, for example, with apparatuses as shown in FIGS. 2 to 4. The apparatus as shown in FIG. 1 is composed of an inlet 2 for supplying exhaust water to be treated, a filtering portion F comprising RCS filter or filters, and a water receiver 3 for receiving the purified water. In a preferred embodiment as shown in FIG. 2, the apparatus is further composed of a means for supplying the purified water to the filtering portion F, which is connected to the water receiver 3, whereby the purified water is supplied to the filter or filters to recover (activate) the filter(s). In a more preferable embodiment, the apparatus further comprises a water tank 5 having a stirrer 6 in which the exhaust water is pretreated with DCP, and the water tank is connected to the filtering portion F by means of a liquid transfer portion 7 such as a pump.

3) Application to Gas

TABLE 4

Applications (4) of OME/DCP/RCS: Applied to Environmental Fields (Applied to Gases)

| Applicable techniques | Application | Contents |
| --- | --- | --- |
| 12 Deodorization of organic and inorganic gases, Adsorption, absorption and decomposition of harmful substances in gases | OME/DCP/RCS | a. Spraying of OME Diluent<br>b. Application of OME Diluent containing DCP to source of the gas generation<br>c. Passing the gas through RCS filter |

B-12 Absorption, Adsorption, Decomposition and Deodorization of Gas

In this embodiment, bad smells originating from organic compounds, such as bad smells due to rotten animals or plants, due to feces and urine of animals, and methane, mercaptans; bad smells originating from inorganic compounds such as ammonia, and hydrogen sulfide; or harmful substances contained in the atmosphere such as dioxins, PCB, nitrogen oxides can be absorbed, adsorbed, decomposed, and/or deodorized.

The treating processes are roughly divided into (a) a process for spraying OME diluent to a gas; (b) a process for applying DCP introduced into OME diluent to a source of generating a gas; and in the case where the gas to be treated is in a closed environment such as a gas passing through a flue (c) a process for passing the gas through an RCS filter or RCS filters. In the case of treating dioxins, etc., the gas can be similarly treated by means of a mist trap or a process described in Japanese Patent Application No. 9-291467.

C) Other Applications

In addition to the above applications, OME, DCP, and RCS according to the present invention can be used in various forms. Examples are as follows:

Due to its deodorization effect as described above, OME diluent can be incorporated in a spraying container, such as an atomizer, to be used, for example, as a liquid deodorizer in the stockbreeding, household, or chemical industries.

OME diluent can also be incorporated in a spraying container, such as an atomizer, to be used, for example, as an agent for removing photogenic bacteria for plants, and as an activator for plants.

By impregnating wood in OME diluent for a short period, preferably within 1 day, the prevention of insects can be imparted to the wood. In this case, care should be taken since the cellulose in the wood starts to decompose if the wood is impregnated in OME diluent for a prolonged period of time.

DCP, RCS or a mixture thereof can be used as a powdery deodorizer for a refrigerator or shoes.

Since RCS possesses the function of removing harmful substances, particularly chlorine and the sterilizing function at the same time, the filter in which RCS is introduced can be used as a filter for a water purification apparatus for drinking or as a filter for showering with the introduction of a shower head, or as a filter for an air conditioner.

DCP can be introduced into a non-woven fabric, for example into a bag such as a tea bag, to be used as a purifier for a water tank, a pond, or a bath.

Concrete formed from fine aggregations containing DCP may be used to in the construction of a water tank, a construction for conditioning water properties.

Furthermore, when RCS is used in a material as the filter for a purifier of an ornamental water tank, a transparent state can be maintained over 1 month without changing the water.

EXAMPLES

The present invention will now be described in more detail by referring to Examples, which do not restrict the scope of the present invention.

Example 1 Production OM/OME

To an organism-activating agent, marketed under the trade name of VITARY AMINON from ORIENT GREEN CO. LTD, were added 5% by weight of humus based on broad-leaf trees as a source of aerobic microorganisms and 5% by weight of extract of Basidiomycetes obtained by mating *Pleurotus coruncopiae* with Pleurotus coruncopiae to carry out the culture over a period of 30 days under aeration conditions at normal temperature and normal pressure. At the start of the culturing, the culture had smells, but 30 days after the culturing has began, the smell had disappeared from the culture.

After this 30-day period, the aeration was terminated, and 5% by weight of sludge from sewage as a source of anaerobic microorganisms was added per ton of the culture to continue the culturing over a period of 30 days at normal temperature and normal pressure. Similarly, the smells from the sewage had disappeared after this 30 days.

Photosynthesis bacteria available from ORIENT GREEN CO. LTD under the trade names of GREEN AMINON and RED AMINON were added to the culture each in an amount of 1.5 liter per ton of the culture to continue the culturing over a period of another 30 days. This produced OM liquid.

Moreover, carbon power (10 kg) was added to the OM liquid and the culturing was continued for another 60 days, at which time the carbon power was observed to be decomposed.

The culture obtained as described above was diluted three times with the OM liquid which had been previously obtained to produce OME liquid.

According to a standard for toxicity of chemical products (1987), OME is tested for oral acute toxicity in mice. When OME was administrated to mice at the maximum dosage of OME defined in this standard (2 ml per 100 g weight (20 m/kg)), no mice died. Consequently, the lethal dose in the sample mice was determined to be greater than 20 ml/kg both in the case of males and females.

Comparative Example 1

Production of Comparative Culture

A culture containing both aerobic bacteria and anaerobic bacteria described in Japanese Patent Application No. 9-291467 was produced with the same method as in Example 1 except that there was no introduction of basidiomycetes.

When carbon powder was added to the resulting culture, no decomposition of carbon powder was found.

Example 2

PRODUCTION OF DCP

Carbon from plants having been burned at a low temperature was impregnated in an aqueous solution in which OME obtained from Example 1 was diluted 1000 times with water. After about 3 to 7 days, the carbonaceous substances became muddy to give DCP. (DCP slurry). The DCP slurry was spontaneously dried to give DCP powder.

Similarly, when the carbon having been burned at a low temperature was impregnated in an aqueous solution in which the culture obtained from Comparative Example 1 was diluted 1000 times with water, the carbonaceous substance was not changed even after 30 dyas.

Example 3

PRODUCTION OF RCS

Activated carbon was impregnated in the OME liquid obtained from Example 1 for 3 to 7 days to produce RCS.

Applications to Agricultural Fields

Example 4, Comparative Example 2, Control 1

Improvement in Sandy Soil Containing Salts

Sandy soil containing salts from the beach of Nijinomatsubara Beach Kaigan, Saga, Japan was improved.

First, the sawdust of needle-leaf trees as a soil base material was laid on the seashore so as to be approximately 5 to 10 cm in height. Slight amounts of chicken droppings were added thereto, and a diluted OME in which OME obtained in Example 1 was diluted 1000 times with water, was sprayed thereon so as to sufficiently wet the soil base material (Example 4). Similarly, a microorganisms' culture conventionally said to have a performance for decomposing cellulose as described in Japanese Examined Patent Publication No. 4-42355 (Comparative Example 2), and the culture from Comparative Example 1 (Comparative Example 3) were sprayed on two respective parts of the soil. As a control soil, only chicken droppings were added (Control 1).

After being left standing for two weeks, tomato, green soybeans, watermelon, pumpkin, eggplant, Brassica campestris, and sweet potato were cultivated on each soil. As a result, good crops could be harvested from the soil of Example 4, but no crop could be harvested from the soils of Comparative Examples 2 and 3, and Control 1.

Example 5, Comparative Examples 4 and 5, Control 2

Treatment of Various Soils

As for sandy soil composed of commercially available sands, soils whose crumb structure had been lost due to the application of agricultural chemicals, acidified soil, and burned soil, similar bacterial treatments were carried out in the same manners as in Example 1, Comparative Examples 2 and 3 and Control 1, respectively, and the crops were cultivated. As a result, good crops could be harvested from the soil of Example 5, but no crop could be harvested from the soils of Comparative Examples 4 and 5, and Control 2.

From these results, it has been understood that the process according to the present invention could exhibit significant effects within a short period of time. It should be noted that the progress of converting the sandy soil into fertilized soil could be observed by the necked eye (approximately 30% of the sands being converted into fertilized soil after three months).

Example 6

Rescue of Plants with Stem Canker and Mottled Spot

An approximately 80 years old Japanese red pine affected with stem canker was dug up, and the affected parts were surgically removed. The whole of the red pine was thoroughly washed with a diluent of OME diluted 1000 times using the OME obtained from Example 1. Thereafter, DCP slurry was applied to the surgically operated portions and then dried. Furthermore, the soil was well washed with the diluent of OME diluted 1000 times using the OME obtained from Example 1. Two hours after the treatment, the appearance of new buds could be observed.

As for an approximately 30 years old pear tree affected with stem canker, a pear tree affected with root rot, an approximately 20 years old apple tree affected with stem canker, and an apple tree affected with root rot, the same treatment as described above was carried out. They were found to form buds after two to three hours.

Example 7

Treatment of Powdery Mildew

In this example, a diluent of OME diluted 1000 times using the OME obtained from Example 1 was used for the treatment. Cucumbers at the final stage of cultivation affected with powdery mildew were treated with the diluent of OME diluted 1000 times using the OME obtained from Example 1. Specifically, the diluent (300 liters) was sprayed on the surfaces of leaves and the soil (8 Acres) for cultivating the cucumbers. After one week, the spread of the powdery mildew was found to be suppressed. Two weeks after the treatment, OME diluent was similarly sprayed on the surfaces of the leaves and soil in an amount of 100 liters. After another one week, the treated plants were able to yield as many cucumbers as those which were not affected with powdery mildew.

Example 8

Extermination of Harmful Insects

In this example, four of greenhouses for strawberries affected with caterpillars of Mamestra brassicae among 20 Acres were treated with a diluent of OME diluted 1000 times using the OME obtained from Example 1 to exterminate the harmful insects. The OME diluent was sprayed onto the surfaces of the leaves and soil in an amount of 200 liters. One week after the spraying, the growth of the plants was observed in comparison with the plant having not yet been treated. At that time, the leaves and stems of the strawberries having been treated were found to be elastic. Three weeks after the treatment, carcasses of the insects were observed. Since damage due to the insects had started in the untreated portions, both OME diluent (350 liters) was sprayed and the OM diluent was sprinkled in an amount of 500 liters over the leaves and soil of all of greenhouses. Similarly, after 1 week, OM diluent was sprayed in an amount of 350 liters to the whole of the houses, and OM diluent was sprinkled in an amount of 500 liters all of greenhouse. It was found that no caterpillars remained.

Application to Environmental Fields: Application to Solids

Example 9

Garbage Treatment

A diluent of OME diluted 1000 times with the OME obtained from Example 1 was applied to a 1:1 mixture of sawdust from needle-leaf trees and chaff, and the mixture was stirred to produce a garbage decomposing material.

A 30-liter volume plastic bucket having a wire net laid on the bottom was filled with approximately 25 liters of the garbage decomposing material. Thereafter, household garbage (3 liters) was incorporated in the bucket and the contents were mixed well. Immediately after the treatment, bad smells from the garbage disappeared, and the garbage perfectly disappeared after 1 to 3 days. On the bottom of the bucket, a liquid due to the fermentation and decomposition of the garage was collected. This liquid contained minerals and could be used as a good liquid fertilizer.

Example 10

Removal of Lead in Burned Ash With OM

Two hundred grams of burned ashes containing approximately 0.6 mg of lead was washed with a diluent produced by diluting 3cc of the OM obtained from Example 1 with 600 cc of water. The washing was repeated twice. As a result, the content of the lead in the burned ashes was decreased to 0.015 mg/l (measured according to JIS K0102 31.2).

Example 11

Removal of Heavy Metals in Burned Ash with OM

The procedure of Example 10 was repeated to remove heavy metals contained in burned ashes shown in Table 5. Table 5 shows the amounts of heavy metals before washing with OME and after the treatment.

TABLE 5

| | Unit: mg/kg | | |
|---|---|---|---|
| Components | Before Treatment | Treated with OM | After Treatment |
| Calcium | 1300000 | 2200 | 16 |
| Iron | 23000 | 19 | N.D. |
| Sodium | 13000 | 570 | 14 |
| Magnesium | 11000 | 24 | 2.6 |
| Zinc | 3500 | 11 | 0.06 |
| Copper | 2400 | 7.7 | 0.02 |
| Lead | 1100 | 7.2 | N.D |
| Cadmium | 9.7 | 0.05 | N.D |

*Determined by an atomic absorption process
**N.D. means not determined.

Liquid Treatment

Example 12

Removal of Water Bloom

Onto and into water containing water bloom, such as a water reservoir for hydroponics, a river into which exhaust water from pig breeding was spilt, and a pond of a golf course, a diluent of the OME obtained from Example 1 diluted 1000 times with water was sprayed. Immediately after spraying, the water blooms were instantly removed.

Example 13

Decomposition of Azo Dyestuffs

Into 2-liter volume transparent containers was incorporated approximately 1 liter of tap water each, and 1 g of azo dyestuff such as indigo dyestuff, an orange dyestuff, a red dyestuff, a yellow dyestuff, or a blue dyestuff was added respectively. The contents were thoroughly stirred to prepare a sample exhaust waters. To each of the samples was added 3 mg of DCP. When each container was stirred by means of a magnet stirrer, the samples were found to become perfectly colorless after 2 to 5 minutes. BOD/COD measurement showed that BOD having having 650 before treatment was reduced to be not more than 5, and approximately COD having 450 was reduced to be not more than 5, after the treatment respectively.

Example 14

Treatment of Photographic Exhaust Water

Exhaust water (1 liter) containing cyan, acetic acid, and mercury from a small-scale photo finishing service shop was incorporated in a 2-liter volume transparent container, 3 mg of the DCP obtained in Example 2 was incorporated, and the mixture was stirred with a magnet stirrer for 10 minutes. The treatment removed harmful substances and the exhaust was perfectly deodorized. Thereafter, the exhaust water treated with DCP was passed through a funnel filled with the RCS obtained in Example 3. The results of measuring the total nitrogen content, BOD, and COD before treatment, after the treatment with DCP, and after the treatment with RCS are shown in Table 6.

TABLE 6

| | (mg/l) | | | |
| --- | --- | --- | --- | --- |
| | Before treatment | Treated with DCP | Treated with RCS | Method |
| BOD | 200 | 26 | 5 | JIS K 0102 21 32.3 |
| COD$_{Mn}$ | 16000 | 1300 | 23 | JIS K 0102 17 |
| All nitrogen | 8900 | 1200 | 7.0 | JIS K 0102 45.2 |

Example 15

Treatment of Polluted Area of Water

Water (1 liter) containing seston and polluted sludge from a lake or a marsh was incorporated in a 2-liter volume transparent, container, 3 mg of the DCP obtained in Example 2 was incorporated, and the mixture was stirred with a magnet stirrer for 10 minutes. The water after the treatment had become perfectly colorless. The polluted sludge was gradually decomposed after the treatment, and could not be observed by the necked eye after 1 month.

Example 16

Treatment of Exhaust Water from Sewage

Water (1 liter) from exhaust water from sewage having been filtered through a filter was incorporated in a 2-liter volume transparent container, 3 mg of the DCP obtained in Example 2 was incorporated, and the mixture was stirred with a magnet stirrer for 10 minutes. The water after the treatment had become perfectly colorless. The water giving off a sickening smell before the treatment was deodorized by incorporating DCP followed by stirring to an extent where no smell was noticable.

Example 17

Exhaust Liquid Containing PCB

The same treatment as in Example 16 was carried out using an exhaust liquid containing 40000 mg/liter of PCB. As a result, the content of PCB was reduced to be 0.1 ppm.

Example 18

Exhaust Liquid from Plating

The same treatment as in Example 16 was carried out using a lead acetate exhaust liquid having 22000 ppm of COD, a Pb content of 164000 ppm and a pH level of 8.7. As a result, COD was reduced to 320 ppm, but the precipitation of Pb was observed. When the same procedure was repeated one more time, the content of Pb was found to be from 1 to 2 ppm and COD was found to be further reduced to 4 ppm, and the pH level also became 7.7.

Example 19

Conversion of Seawater into Freshwater

Seawater (10 liter) from Sagami Bay was incorporated in a mixer, 3 g of DCP was incorporated with stirring, and the stirring of the mixture was continued for approximately 30 seconds. As a result, the salts in the seawater were found to be reduced approximately 80%.

The seawater treated as described above was passed through a filter with which the RCS obtained in Example 3 was filled to perfectly remove the salts. The results are shown in Table 7. When this experiment was repeated several times, similar results were obtained.

TABLE 7

| | | Before treatment | After treatment | Method |
| --- | --- | --- | --- | --- |
| Cl | 17 g/L | 240 mg/L | | JIS K 0102-35-1 |
| Na$^+$ | 13 g/L | 90 mg/L | | JIS K 0102-48-2 |

Example 20

Treatment of Salted Plum Juice

To exhaust water (1 ton) containing salted plum juice exhausted in the course of producing pickled plums and having the following characteristics was added 4 liters of the DCP obtained in Example 2, and the mixture were well stirred. The mixture was filtered once through sand, and then twice through a filter which was filled with 4 liters of the RCS obtained in Example 2. The results are shown in Table 8.

TABLE 8

| | Before Treatment | After Treatment |
| --- | --- | --- |
| Titrated Acidity (as Citric Acid) | 30.02 g/L | ND |
| Sugar Content | 30.1 | 0 |
| Ca | 296 mg/L | ND |
| Na | 43.3 g/L | 39 mg/L |
| Salt (as Na) | 113 g/L | 99 mg/L |
| K | 2.05 g/L | 30 mg/L |
| Mg | 161 mg/L | ND |
| Sucrose | 3.14% | ND |
| BOD | 160000 mg/L | 13 mg/L |
| COD | 120000 mg/L | 16 mg/L |
| pH | 2.6 (20 C) | 6.3(21 C) |

From the results shown in Table 8, it can be understood that DCP effectively functioned even at a pH level of 2.6, and had functions for reducing BOD and COD.

Example 20

Treatment of Exhaust from Plating

Into a plating mixed bath composed of 100 ml of nickel plating liquid (Watt bath), 100 ml of soldering bath, 100 ml of electrolytic copper bath, 100 ml of an alkaline degreasing liquid (Ace Clean 200 10 solution), 100 ml of 5% sodium tertiary phosphate solution, and 100 ml of 5% sulfuric acid diluted with 2 liters of tap water, 10 g of the DCP obtained in Example 2 was incorporated, and the liquid was filtered through a filter containing the RCS obtained in Example 3. The results are shown in Table 9.

TABLE 9

| Type Exhaust Water | pH | $COD_{Mn}$ | Pb |
|---|---|---|---|
| Lead Acetate Exhaust Water | 3.7 | 22000 | 164000 |
| After Treatment | 6.7 | 3 | 1 or less |
| Nylon Exhaust Water | 10.6 | 284000 | None |
| After Treatment | 6.4 | 8 | None |

Example 21

Treatment of Exhaust Liquid Containing Harmful Substances

Into a liquid, which was expelled from a plant after final treatment of its industrial waste, containing the following substances, 10 g of the DCP obtained in Example 2 was incorporated, and then the liquid was passed twice through a filter containing the RCS obtained in Example 3. The results are shown in Table 10.

TABLE 10

(mg/L)

| Harmful Substances | Before Treatment | Treated with DCP |
|---|---|---|
| Tetravalent Chromium Compounds | 0.6(T—Cr) | — |
| 1,1-dichloroethylene | 0.02 | — |
| Living Environment | | |
| pH | 7.16(25° C.) | 5.84 |
| BOD | 22300 | 5.15 |
| COS | 3640 | 5.00 |
| SS | 271 | — |
| n-Hexane Extract | 0 | — |
| - (Mineral Oils) | 3.4 | — |
| - (Vegetable/Animal Oils) | 338 | 2.42 |
| N | 1.6 | — |
| P | 5.02 | — |
| F | 0.6 | — |
| Cr | 1.75 | — |
| Soluble Fe | 1.72 | — |
| Soluble Mn | 23.0 | — |
| Phenol | <1.0 | — |
| Cu | 0.43 | — |
| Zn | | |
| Others | | |
| $NH_4^+$—N— | 3170 | — |
| $Cl^-$ | 28900 | 90. |
| $Na^+$ | 11200 | 10.1 |
| Ca | 1830 | — |

Applications to Gases

Example 22

Removal of Odors Oriented from Rotten Proteins

Rotten Washington clams were introduced in a conical flask. Subsequently, an untreated sample and a sample treated by dropping a drop of a 1000 times diluent of the OM obtained in Example 1 were collected in bags by means of a sampling pump. The collected samples are measured by a gas detector (Kitagwa Type). The results are shown in Table 11.

TABLE 11

| | Before | After |
|---|---|---|
| Hydrogen Sulfide | 400 ppm | N.D. |
| Methylmercaptan | 120 ppm | N.D. |
| Propylene | 60 ppm | N.D. |
| Ethylmercaptan | 3 ppm | N.D. |

Example 22 and Comparative Example 6

A Comparison of Gas Adsorption of RCS with that of Activated Carbon

Formadehyde and ammonia were adsorbed in the RCS obtained in Example 3 and untreated activated carbon to compare their adsorption performances. The results are shown in FIG. 4.

It is clear from FIG. 4 that the adsorption performances of these substances in RCS are significantly higher than those of untreated RCS.

INDUSTRIAL APPLICABILITY

As described above, the present invention has the following excellent advantages.

A microorganism culture containing aerobic microorganisms, anaerobic microorganisms, at least one Basidiomycetes belonging to Pleurotus coruncopiae living in symbiosis with each other, and enzymes produced as their metabolites, a carrier obtained by absorbing the active components of the culture on the finely pulverized carbon, and a porous absorbing material having the active components of the culture adsorbed thereon has capabilities of absorption, adsorption, decomposition, deodorization, decoloring of harmful substances and, thus, they can be used in various agricultural fields and environmental fields.

What is claimed is:

1. An enzyme/microorganism composite solution comprising a symbiotic culture of
   (a) aerobic microorganisms,
   (b) anaerobic microorganisms, and
   (c) at least one Basidiomycetes belonging to Pleurotus coruncopiae, and enzymes produced as their metabolites,
   wherein said composite solution is prepared by
     i) incorporating a source of the aerobic microorganisms and an essence of the at least one Basidiomycetes containing at least Pleurotus coruncopiae into a solution, said solution obtained by
        (a) pulverizing proteins mainly comprising consisting essentially of animal proteins to obtain pulverized proteins,
        (b) adding grain and yeast to the pulverized proteins to undergo fermentation and to obtain a fermented product,
        (c) heating the fermented product to obtain a heated product,
        (d) pulverizing the heated product to obtain a pulverized product,
        (e) adding a Lactobacillaceae culture or a Bacillus subtilis culture to the pulverized product and fermenting under aerobic conditions at room temperature and atmospheric pressure until the solution becomes transparent, and ii) incorporating a source of the anaerobic microorganisms to the solution and culturing the solution under anaerobic conditions at normal temperature and normal pressure to obtain the composite solution.

2. The composite solution as claimed in claim 1, wherein the Basidiomycetes is obtained by mating *Pleurotus coruncopiae* with *Pleurotus coruncopiae*.

3. The composite solution as claimed in claim 1, comprising a photosynthetic bacteria.

4. The composite solution as claimed in claim 3, comprising enzymes for decomposing carbon.

5. A process for producing an enzyme/microorganism composite solution as claimed in claim 1, wherein said process comprises
   i) incorporating a source of aerobic microorganisms and an essence of at least one Basidiomycetes containing at least *Pleurotus coruncopiae* into a solution, said solution obtained by
      (a) pulverizing proteins consisting essentially of animal proteins to obtain pulverized proteins,
      (b) adding grain and yeast to the pulverized proteins to undergo fermentation and to obtain a fermented product,
      (c) heating the fermented product to obtain a heated product, (c) heating the fermented product to obtain a heated product,
      (d) pulverizing the heated product to obtain a pulverized product,
      (e) adding a Lactobacillaceae culture or a *Bacillus subtilis* culture to the pulverized product and fermenting under aerobic conditions at normal temperature and normal pressure until the solution becomes transparent, and
   ii) incorporating a source of anaerobic microorganisms to the solution and culturing the solution under anaerobic conditions at normal temperature and normal pressure to obtain the composite solution.

6. The process as claimed in claim 5, comprising adding photosynthetic bacteria to the solution and culturing.

7. A soil improving material comprising a microbiological enzyme/microorganism composite solution according to claim 1, and a fibrous substance originating from plants.

8. The soil improving material as claimed in claim 7, wherein said fibrous substance originating from plants is sawdust of needle leaf trees, pulverized substances of logged trees, rice chaff, buckwheat chaff, construction material having been primarily treated, or a mixture thereof.

9. A process for improving soil comprising preparing a mixture comprising a soil improving material comprising a microbiological enzyme/microorganism composite solution according to claim 1, a fibrous substance originating from plants, and a fertilizer, and distributing the mixture on the soil to be treated at a height of from 1 to 100 cm.

10. The process as claimed in claim 9, wherein the soil to be treated is soil having reduced crumb structure.

11. The process as claimed in claim 9, wherein the soil to be treated is desertified soil or soil containing salts.

12. A process for improving soil which comprises placing a fibrous substance originating from plants mixed with a fertilizer at a height of from 1 to 100 cm, and spraying an enzyme/microorganisms composite solution according to claim 1 or the composite solution diluted with water.

13. The process as claimed in claim 12, wherein the soil to be treated is soil having reduced crumb structure.

14. The process as claimed in claim 12, wherein the soil to be treated is desertified soil or soil containing salts.

15. A process for optimizing cultivation of a plant system, wherein the plant system comprises a container for cultivating a plant, a medium for cultivating a plant, and a plant to be cultivated, and wherein the process comprises:

a) incorporating said plant system into a sealed container, b) filling the sealed container with an enzyme/microorganism composite solution according to claim 1 diluted with water, c) sealing the sealed container, and d) decontaminating the sealed container of step c) for a period sufficient for killing disease carriers and eggs thereof existing in the system, and improving cultivation thereby.

16. The process as claimed in claim 15, for reviving a withered plant.

17. A process for reviving a plant infected by a pathogenic organism comprising:

(a) exhuming the plant and washing the entire plant with an enzyme/microorganisms composite solution according to claim 1 diluted with water, (b) spraying the composite solution diluted with water for decontaminating soil from where the plant is exhumed, and (c) replanting the plant and applying the soil from step (b).

18. The process as claimed in claim 17, wherein said pathogenic organism causes drop, clubroot, mottled spot, brown canker, mildew and rust.

19. An organic fertilizer comprising an admixture of feces and urine of livestock, and a solution according to claim 1 diluted with water.

20. The organic fertilizer as claimed in claim 19, further comprising sawdust of needle leaf trees.

21. A garbage decomposing material obtained by impregnating fibrous substances originating from plants with a composite solution according to claim 1.

22. The garbage decomposing material as claimed in claim 21, wherein said fibrous substances originating from plants contain decomposition-resistant substances.

23. A process for odorless decomposition of garbage comprising incorporating into the garbage, a mixture comprising fibrous substances originating from plants and a composite solution according to claim 1, and stirring the mixture to decompose the garbage in an odorless manner.

24. A liquid fertilizer comprising an odorless liquid and obtained by a process for odorless decomposition of garbage comprising incorporating into the garbage, a mixture comprising fibrous substances originating from plants and a composite solution according to claim 1, stirring the mixture to decompose the garbage in an odorless manner and forming a liquid fertilizer from the decomposed garbage, and removing the liquid fertilizer.

25. A process for treating a gas which comprises contacting the gas with a composite solution according to claim 1 diluted with water.

26. The process as claimed in claim 25, wherein the gas is an odorous gas derived from organic or inorganic compounds or a gas containing organic or inorganic chemical hazards.

27. A deodorizer comprising a composite solution according to claim 1 diluted with water.

28. A liquid agent for decolorization of a liquid comprising a composite solution according to claim 1 diluted with water.

29. A process for removing harmful substances from a construction material comprising spraying or impregnating the construction material with a composite solution according to claim 1 diluted with water.

30. A mildew-proofing agent comprising a composite solution according to claim 1 diluted with water.

31. An agent for reviving plants comprising a composite solution according to claim 1 diluted with water.

* * * * *